United States Patent [19]
Jørgensen

[11] Patent Number: 6,100,063
[45] Date of Patent: Aug. 8, 2000

[54] PROCARYOTIC CELL COMPRISING AT LEAST TWO COPIES OF A GENE

[75] Inventor: Steen Troels Jørgensen, Allerød, Denmark

[73] Assignee: Novo Nordisk A/S, Bagsvaerd, Denmark

[21] Appl. No.: 09/248,643

[22] Filed: Feb. 11, 1999

Related U.S. Application Data

[60] Provisional application No. 60/074,704, Feb. 13, 1998.

[30] Foreign Application Priority Data

Feb. 12, 1998 [DK] Denmark ................................ 0201/98

[51] Int. Cl.⁷ ..................................................... C12P 21/02
[52] U.S. Cl. ......................... 435/69.1; 435/477; 435/183; 435/252.31
[58] Field of Search ................................. 435/69.1, 477, 435/183, 252.31

[56] References Cited

U.S. PATENT DOCUMENTS

| | | | |
|---|---|---|---|
| 5,460,954 | 10/1995 | Lee et al. | 435/69.5 |
| 5,789,208 | 8/1998 | Sharon | 435/91.41 |

FOREIGN PATENT DOCUMENTS 0 284 126 B1  9/1988  European Pat. Off. .

*Primary Examiner*—James Ketter
*Attorney, Agent, or Firm*—Steve T. Zelson, Esq.; Reza Green, Esq.

[57] ABSTRACT

A prokaryotic cell expressing a gene of interest and comprising at least two copies of said gene on the chromosome.

10 Claims, 29 Drawing Sheets

Parallel transcription of two copies of a gene

A:

Homologous cross out

Divergent transcription of two copies of a gene

B:

NO homologous cross out

Convergent transcription of two copies of a gene

C:

NO homologous cross out

PROCARYOTIC CELL COMPRISING AT LEAST TWO COPIES OF A GENE

CROSS-REFERENCE TO RELATED APPLICATIONS

This application claims priority under 35 U.S.C. 119 of Danish application 0201/98 filed Feb. 12, 1998, and of U.S. provisional application 60/074,704 filed Feb. 13, 1998, the contents of which are fully incorporated herein by reference.

FIELD OF INVENTION

A prokaryotic cell expressing a gene of interest and comprising at least two copies of said gene on the chromosome.

BACKGROUND OF THE INVENTION

Prokaryotic multicopy production cells, i.e. cells comprising more than one copy of a gene of interest, have been used for production of proteins of interest at industrial scale.

Preferred multicopy production cells are cells which stabile maintain the individual copies of the genes of interest during fermentation.

Further, due to environmental concerns there is an increasing desire for production cells which do not comprise any integrated antibiotic resistance genes on the chromosome and according to this line production cells which are capable of stabile maintaining the copies of the gene of interest in a fermentation medium NOT comprising an antibiotic.

EP 284126 describes a solution to the stability issue above by providing a method for constructing a prokaryotic cell comprising on the chromosome at least two copies of a gene of interest separated by endogenous DNA, which is vital (essential) to the host cell (see claim 1 of EP 284126).

The individual copies of the gene of interest are stabile maintained in a fermented cell population due to the essential DNA. If a cell crosses out this vital DNA by homologous recombination between the two copies of the gene of interest, the cell looses vital DNA and this specific cell will die.

Thereby it is possible to maintain a stable cell population comprising the copies of the gene of interest.

The method requires a knowledge of which DNA regions are vital to the cell. Alternatively, the gene is integrated on very distant places in the chromosome to have a high probability that there would be vital DNA between the copies (see FIG. 2 of EP 284126). This is a relatively laborious process and uncertain process.

SUMMARY OF THE INVENTION

The problem to be solved by the present invention is to provide a prokaryotic cell expressing a gene of interest and comprising at least two copies of said gene on the chromosome.

Further, said prokaryotic cell should be
a) stable in the sense that during fermentation it is able to maintain two copies of the gene on the chromosome; and
b) able to stably maintain the two copies of the gene without having a DNA segment, situated between the two copies of the gene, which segment is essential for the growth of the cell as described in e.g. EP 284126.

The solution is based on that the present inventor has identified that it is possible during fermentation to stably maintaining two anti-parallelly transcribed copies of a gene on the chromosome of a cell (see FIG. 1) and the two anti-parallelly transcribed genes can be stably maintained even without having a DNA segment, situated between the two copies of the gene, which is essential for the growth of the cell.

Accordingly, in a first aspect the present invention relates to a prokaryotic cell expressing a gene of interest characterised in that,
 i) the cell comprises on the chromosome two anti-parallelly transcribed copies of said gene of interest; and
 ii) any DNA segment situated between the two copies of the gene of interest under item i) only comprises a DNA sequence which is not essential for the growth of the cell.

In a second aspect the present invention relates to a method for constructing a prokaryotic cell expressing a gene of interest comprising the construction of a cell wherein
 i) the cell comprises on the chromosome two anti-parallelly transcribed copies of said gene of interest; and
 ii) any DNA segment situated between the two copies of the gene of interest under item i) only comprises a DNA sequence which is not essential for the growth of the cell.

In a third aspect the invention relates to a method for production and isolation of a polypeptide of interest, comprising
 i) culturing a prokaryotic cell according to the first aspect of the invention under suitable conditions permitting expression of the polypeptide of interest encoded by the gene of interest; and
 ii) isolating the polypeptide of interest.

One of the advantages of a prokaryotic cell, as described herein, is that said two copies of a gene are anti-parallelly transcribed (i.e. either convergently or divergently transcribed), which minimises the risk that one copy of said gene will be lost from the cell by homologous recombination, as compared to when the genes are parallelly transcribed (see FIG. 1 for illustration).

This implies a further advantage of said prokaryotic cell, since it is then possible to have a stable integration of said two copies of a gene, without having a DNA segment situated between the two copies of said gene, which are essential for the growth of the cell.

Accordingly, there is no need for integrating the individual copies of the gene of interest at very distant places on the chromosome as described in EP 284126 (see FIG. 2 of EP 284126). This makes it relatively simpler to construct a prokaryotic cell (as described herein) as compared to the construction of a cell of EP 284126. See below for further details on preferred ways of construction of a prokaryotic cell as described herein.

Further, in the art said DNA segment essential for the growth of the cell has been an antibiotic resistance marker gene, which has been used to construct prokaryotic cells comprising more than one copy of a gene of interest (see e.g. EP 166 628 and WO 94/14968).

Accordingly, a further advantage of a method for constructing a prokaryotic cell, as described herein, is that it provides a simple method of producing a prokaryotic cell which expresses a gene from two copies of said gene, without the cell comprising an introduced antibiotic resistance gene.

DEFINITIONS

Before describing the invention in details, terms of the independent aspects of the invention will be further defined below.

The term "a gene" indicates herein a gene (a DNA sequence) will is capable of being expressed into a polypeptide within said cell. Accordingly, said gene sequence will be defined as an open reading frame starting from a start codon (normally "ATG", "GTG", or "TTG") and ending at a stop codon (normally "TAA", "TAG" or "TGA").

In order to express said gene there must be elements, as known in the art, in connection with the gene, necessary for expression of the gene within the cell. Such standard elements may include a promoter, a ribosomal binding site, a termination sequence, and may be others elements as known in the art.

The term "two anti-parallelly transcribed copies of said gene" denotes herein that said the genes are either convergently or divergently transcribed, i.e. present in opposite orientation relative to each other. See FIG. 1 for a graphic illustration.

The term "the cell comprises on the chromosome two anti-parallelly transcribed copies of said gene of interest", in connection with a prokaryotic cell according to the invention, indicates that said prokaryotic cell comprises at least said two copies of the gene of interest situated as described in the first aspect of the invention. Besides these two copies of said gene of interest said prokaryotic cell may comprises further copies of said gene on the chromosome.

Said further copies may be two further copies of said gene situated according to the invention on a distinct place on the chromosome, or may be just single copy/copies of said gene situated on another part of the chromosome.

The term "a DNA segment which only comprises a DNA sequence which is not essential for the growth of the cell" indicates a DNA segment that if it is crossed out (deleted) from the chromosome of said cell, then the cell is still capable of growing at substantially the same growth rate, under similar growth conditions, as compared to before said DNA segment was deleted.

In contrary when a DNA segment is termed "essential for growth of the cell" this indicates than if said DNA segment is deleted from the cell then said cell will NOT be capable of growing at substantially the same growth rate, under similar growth conditions, as compared to before said DNA segment was deleted.

Such an essential DNA segment, may be a part of the parental (wild-type) chromosomal sequence (as e.g. described in EP 284126), or may be an selectable marker gene, such as an antibiotic resistance marker gene, wherein said selectable marker may have been introduced on the chromosome (see e.g. EP 166628; WO 9414968).

Embodiment(s) of the present invention is described below, by way of examples only.

DRAWINGS

Figure 1:
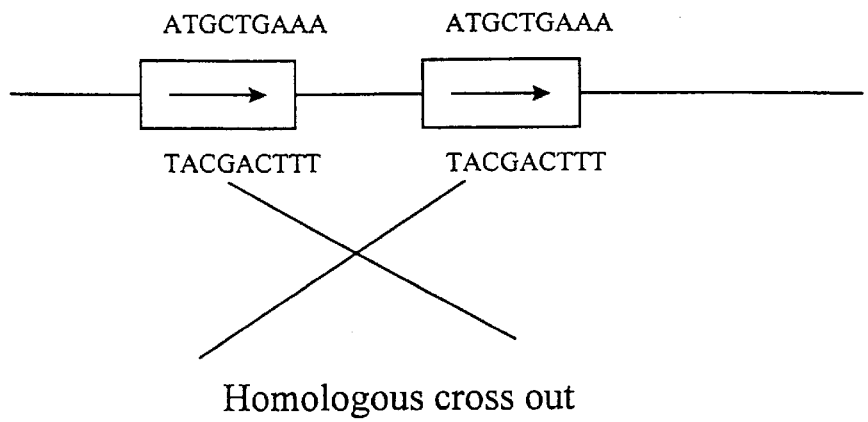
FIG. 1A illustrates two genes, situated on the chromosome of a cell, which are parallelly transcribed. As shown by crossed lines one copy of said gene may be lost from the cell by homologous recombination of the identical DNA sequences.
FIG. 1B illustrates two genes, situated on the chromosome of a cell, which are divergent transcribed. In this situation no direct identical sequences are found between the two genes, consequently, the risk of homologous recombination between the two genes, leading to the loss of one of the gene copies, is drastically minimised.
FIG. 1C illustrates two genes, situated on the chromosome of a cell, which are convergent transcribed. As for part B there is no homologous recombination between said two genes.
Figure 1:
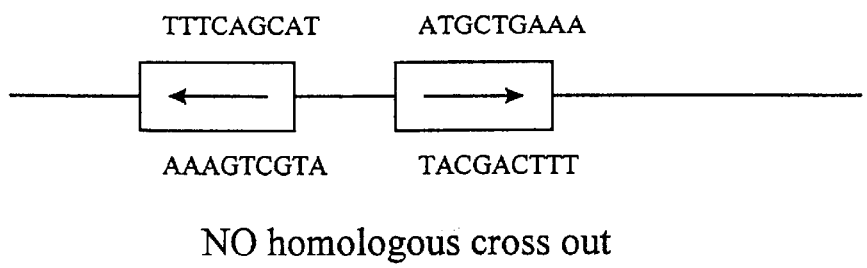
Figure 1:
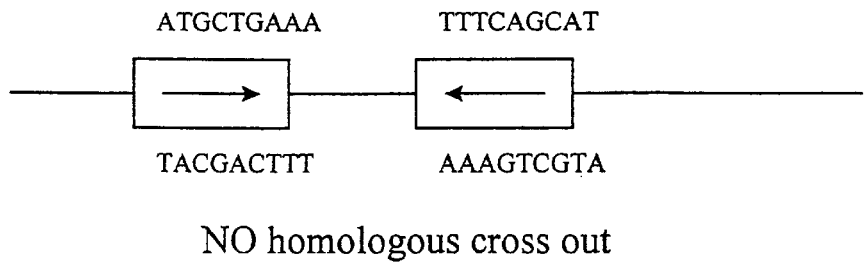

FIG. 2:

This Figure illustrates a preferred strategy to construct a prokaryotic cell as described herein.

Part A:

The DNA segments "ABC" and "DEF" are on the chromosome within the cell.

The DNA segments "ABC", "123", "456", "XXX" (gene of interest), and "DEF" are introduced into the cell, preferably on a temperature sensitive plasmid.

Part B:

After homologous recombination between the DNA segments "ABC" and "DEF" the chromosome now comprises "ABC", "123", "456", "XXX", and "DEF".

A new plasmid in then transformed into the cell comprising the segments "123", "XXX", and "456", wherein the gene "XXX" is transcribed in opposite direction as compared to part A.

Part C:

After homologous recombination between the DNA segments "123" and "456" the chromosome now comprises "ABC", "123", "XXX" "456", "XXX", and "DEF", wherein the genes of interest "XXX" are anti-parallel transcribed. In the specific example shown here they are divergently transcribed.

FIGS. 3–14:

Those Figures show plasmids used in working examples 1 to 3 herein to make a prokaryotic cell, according to the invention, by a method for constructing a prokaryotic cell, according to the invention.

Consequently, reference is made to examples 1 to 3, for further description of said plasmids.

FIGS. 15–29:

Those Figures illustrate strategies and plasmids used in working example 4 herein to make a prokaryotic cell, according to the invention, by a method for constructing a prokaryotic cell, according to the invention.

Consequently, reference is made to example 4, for further description of those Figures.

DETAILED DESCRIPTION OF THE INVENTION

In an embodiment of the invention the gene of interest, according to the aspects of the invention described above, is a gene which is capable of expressing a polypeptide which are secreted from the cell.

Such a gene may preferably encode a fusion polypeptide comprising a signal peptide and the secreted mature polypeptide. Such signal peptides are well known in the art.

In a further embodiment of the invention, said gene encodes an enzyme. Such an enzyme may be an protease, amylase, cellulase, lipase, xylanase, phytase, and other enzymes known in the art.

In an even further embodiment of the invention, said prokaryotic cell is a gram positive prokaryotic cell, such as a Bacillus cell or a Streptomyces cell.

Preferred Bacillus cells are species such as *Bacillus subtilis, Bacillus licheniformis, Bacillus lentus, Bacillus alkalophilus, Bacillus amyloliquefaciens, Bacillus clausii, Bacillus circulans*, and a *Bacillus thuringiensis* cell.

Further, an embodiment of the invention relates to that said DNA segment, which is situated between two copies of said gene, is at least 10 bp long, more preferably from 10 bp to 6000 bp, and even more preferably from 75 bp to 4500 bp long.

An further embodiment of the invention relates to that said DNA segment, which is situated between two copies of said gene, further does not comprise a gene encoding a screenable protein, such as a Green Fluorecent protein (GFP). Such a screenable protein may be used to construct a prokaryotic cell comprising more than one copy of a gene of interest (see DK 0792/97; and WO 99/01562 for a further description of such screenable proteins).

An even further embodiment of the invention relates to a prokaryotic cell of the first aspect of the invention or a method of the second aspect of the invention, wherein said DNA segment, which is situated between the two copies of the gene of interest, does not comprise an antibiotic resistance marker gene, such as an ampicillin resistance gene; an erythromycin resistance gene; a kanamycin resistance gene; a neomycin resistance gene; or a chloramphenicol resistance gene.

See e.g. working example 3 and 4 for examples of such antibiotic resistance marker gene free cells of the invention.

Said method according to the second aspect of the invention and its embodiments described herein may be performed according to any of the in the art known techniques for introducing DNA segments/fragments into the chromosome of a prokaryotic cell, in particular any of the known techniques for introducing said DNA segments into the chromosome by homologous recombination. A preferred strategy is to transform a cell with a plasmid comprising said DNA segment of interest and a temperature sensitive origin of replication. The cell in then cultured a the non-permissive temperature for replication of said plasmid and the plasmid recombine with the chromosome within the cell by homologous recombination.

For further description of such methods reference is made to EP 0 284 126; EP 166 628; WO 94/14968; Maniatis, T., Fritsch, E. F., Sambrook, J. "Molecular Cloning. A laboratory manual". Cold Spring Harbor Laboratories, 1982; Ausubel, F. M., et al. (eds.) "Current Protocols in Molecular Biology". John Wiley and Sons, 1995; Harwood, C. R., and Cutting, S. M. (eds.) "Molecular Biological Methods for Bacillus".

General strategies for performing said method according to the second aspect of the invention and its embodiments described herein are disclosed in working examples herein (see example 3 and 4).

Figure 2:
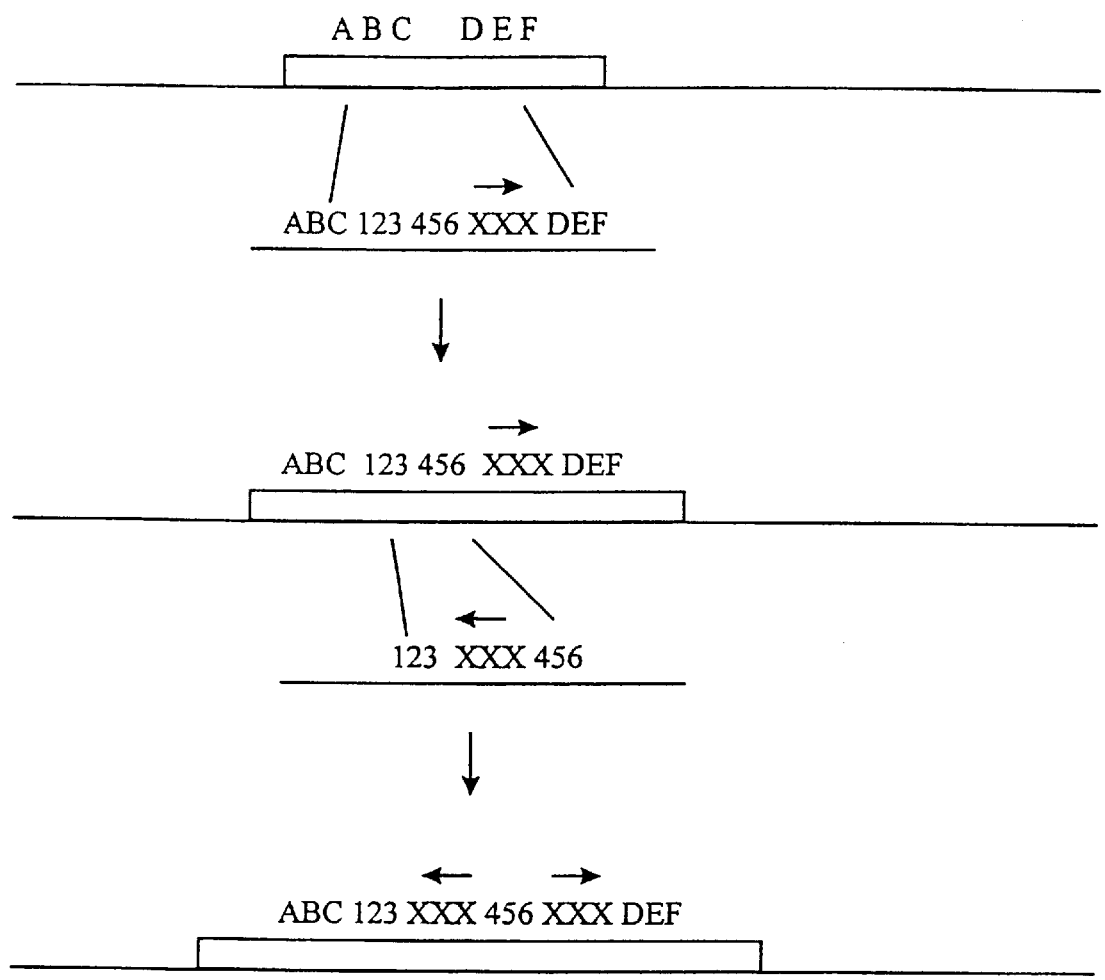

A preferred strategy, based on homologous recombination, is shown in FIG. 2 herein. See working example 4 for an practical example of this strategy.

An advantage of a method as described in a working example herein and as described in FIG. 2, may be that the two copies of the gene of interest are inserted by a precise mechanism into the same locus in the host chromosome. This is preferable if a particularly well-suited locus for such a gene is known.

Accordingly, an embodiment of method for construction a prokaryotic cell expressing a gene, of the invention, is wherein the two copies of the gene of interest are inserted by a precise mechanism into the same locus in the host chromosome.

The specific culturing conditions under step i) and the specific isolation protocol of the polypeptide of interest under step ii) of the method for production and isolation of a polypeptide of interest according to the third aspect of the invention may be performed according to any standard protocol known to the skilled person.

As stated above, an advantage of a prokaryotic cell as described herein is that it is stable in the sense that it during fermentation is able to maintain the two copies of said gene on the chromosome.

Accordingly, it is specially suitable for large scale industrial fermentation's.

Such large scale industrial fermentation's may be characterised by that a) the polypeptide of interest is produced at a relatively high yield or b) that a large scale fermentation process is used.

Consequently, an embodiment of the method for production and isolation of a polypeptide of interest, of the third aspect the invention, is wherein the culturing of a prokaryotic cell of item i) is done under conditions wherein the polypeptide of interest is expresses in an amount of at least 2 g polypeptide (dry matter)/kg culture medium; preferably in an amount of at least 3 g polypeptide (dry matter)/kg culture medium; and most preferably in an amount of at least 5 g polypeptide (dry matter)/kg culture medium.

Further, an embodiment of the method for production and isolation of a polypeptide of interest, of the third aspect the invention, is wherein the culturing of a prokaryotic cell of item i) is in a fermentation process on a volume scale which is >10 $m^3$; preferably >25 $m^3$; more preferably >50 $m^3$; and most preferably >100 $m^3$.

MATERIALS AND METHODS

In vitro DNA work, transformation of bacterial strains etc. were performed using standard methods of molecular biology (Maniatis, T., Fritsch, E. F., Sambrook, J. "Molecular Cloning. A laboratory manual". Cold Spring Harbor Laboratories, 1982; Ausubel, F. M., et al. (eds.) "Current Protocols in Molecular Biology". John Wiley and Sons, 1995; Harwood, C. R., and Cutting, S. M. (eds.) "Molecular Biological Methods for Bacillus". John Wiley and Sons, 1990).

If not otherwise mentioned enzymes for DNA manipulations were used according to the specifications of the suppliers. Media used (TY, BPX and LB agar) have been described in EP 0 506 780. LBPSG agar is LB agar supplemented with phosphate (0.01 M $K_3PO_4$), glucose (0.4%), and starch (0.5%).

EXAMPLE 1

Figure 3:
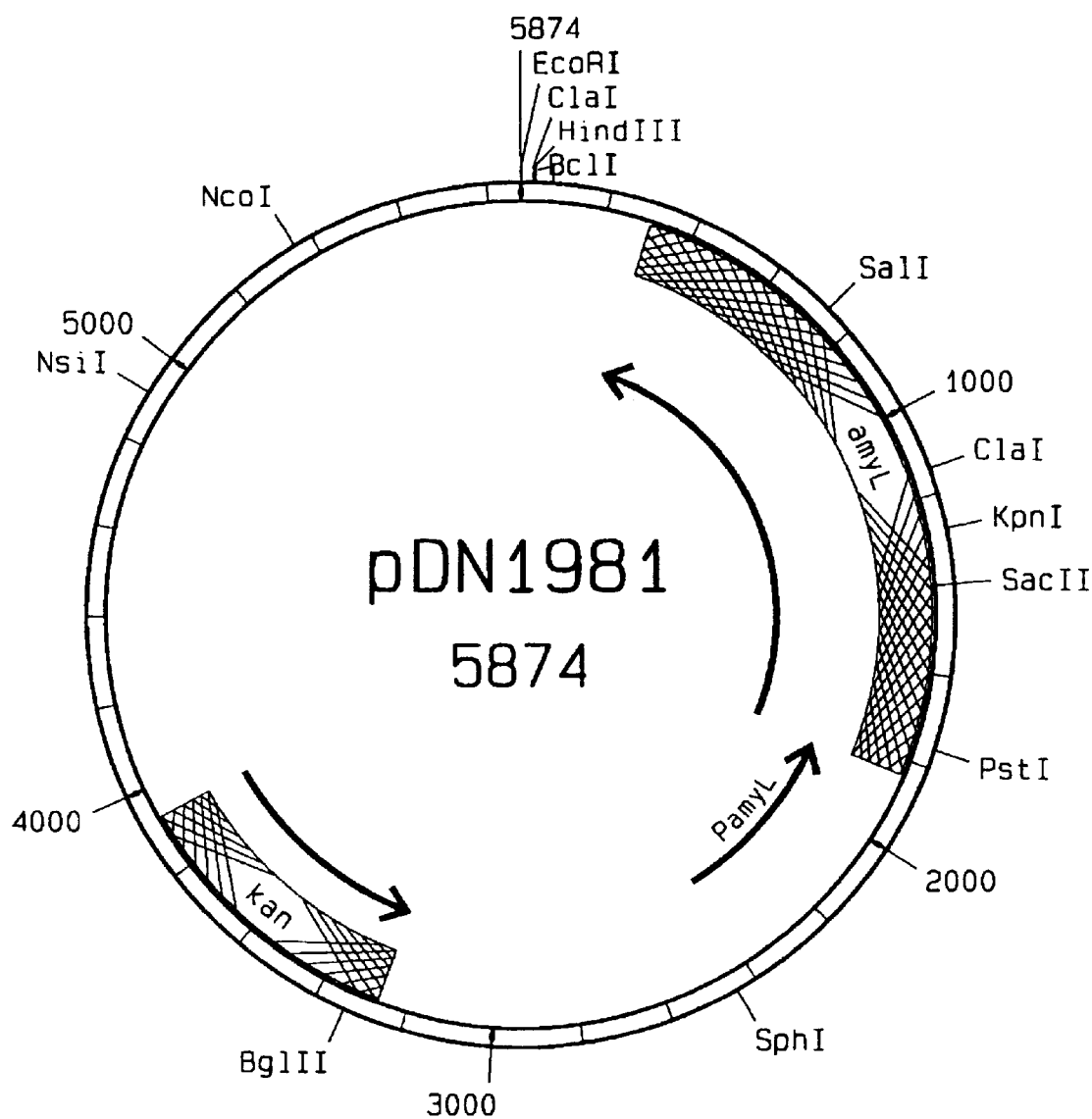
Figure 4:
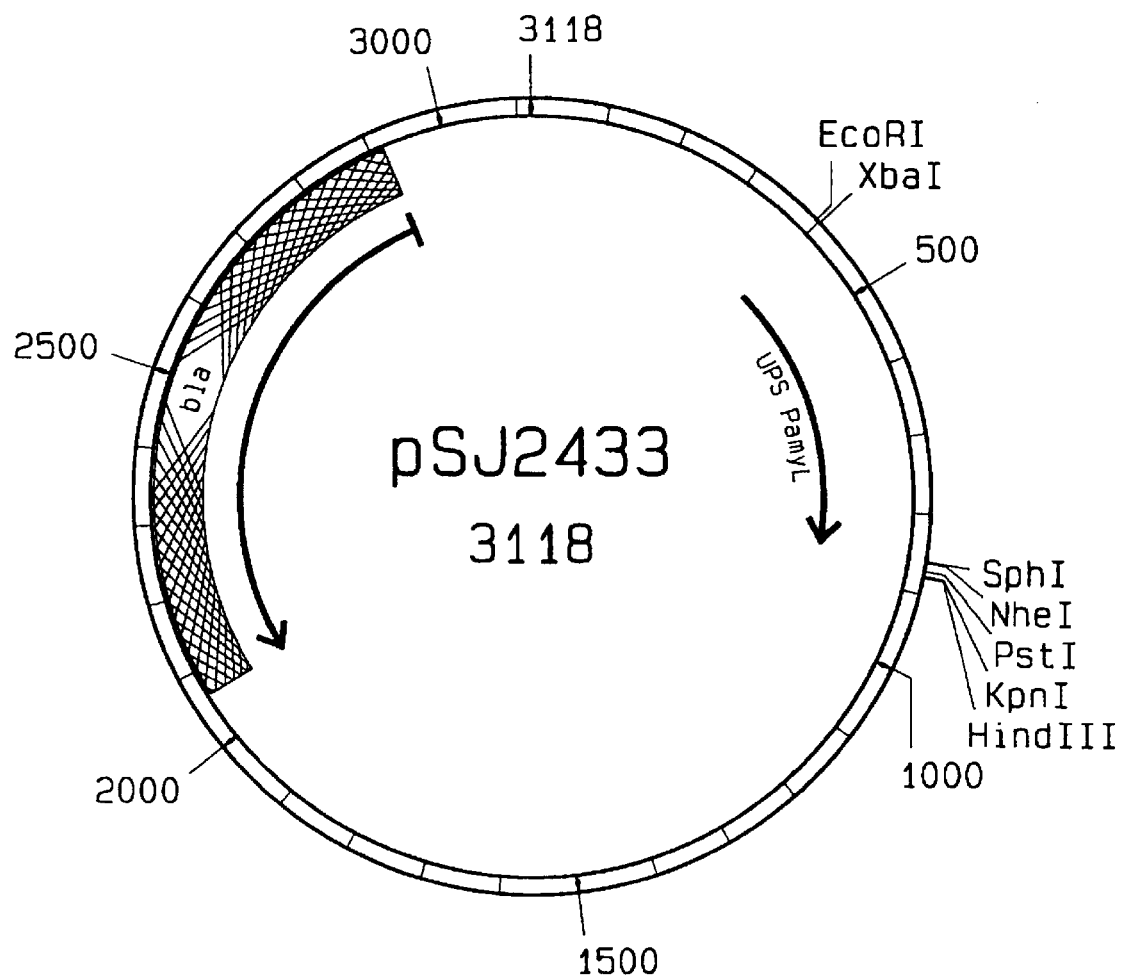

Deletion of the α-amylase (amyL) Promoter from the *B. licheniformis* Chromosome 1A. Plasmid constructions:

The α-amylase (amyL) gene from *B. licheniformis* was cloned on a 2.4 kb SphI-HindIII fragment resulting in plasmid pDN1981 (FIG. 3), as described by Jørgensen et al., 1990. "kan" denotes the pUB110 derived kanamycin resistance gene, and "PamyL" denotes the alpha-amylase promoter region. (Jørgensen, P. L., Hansen, C. K., Poulsen, G. B., Diderichsen, B. (1990). In vivo genetic engineering: homologous recombination as a tool for plasmid construction. Gene 96, 37–41.)

pSJ2433 (FIG. 4) contains the first 450 basepairs of this sequence, denoted UPS_PamyL, cloned into pUC19 (Yanish-Perron et al., 1985 (Yanish-Perron, C., Vieira, J., Messing, J. (1985). Improved M13 phage cloning vectors and host strains: nucleotide sequences of the M13 mp18 and pUC19 vectors. Gene 33, 103–119)), and was constructed as follows: pDN1981 DNA was used as template for PCR amplification with primers LWN4739+LWN4740, the resulting 0.5 kb fragment digested with EcoRI and HindIII, ligated to EcoRI+HindIII digested pUC19, and transformed into *E. coli* SJ2 (Diderichsen et al., 1990 (Diderichsen, B., Wedsted, U., Hedegaard, L., Jensen, B. R., Sjøholm, C. (1990). Cloning of aldb, which encodes α-acetolactate decarboxylase, an exoenzyme from Bacillus brevisl) by electroporation selecting ampicillin resistance (AmpR), 200 μg/ml. "bla" denotes the pUC19 ampicillin resistance gene.

Two transformants were kept as SJ2433 and SJ2434. Identity of the insert was confirmed by DNA sequencing of the ends, but the entire insert was not sequenced.

```
LWN4739

HindIII KpnI  PstI  NheI  SphI <---- amyLV2 464-437------->
5'-TGAGTAAGCTTGGTACCCTGCAGGCTAGCGCATGCGCTGAGATACAGTTACCAATTGATAGCC-3'  (SEQ ID NO:1)

LWN4740

Figure 5:
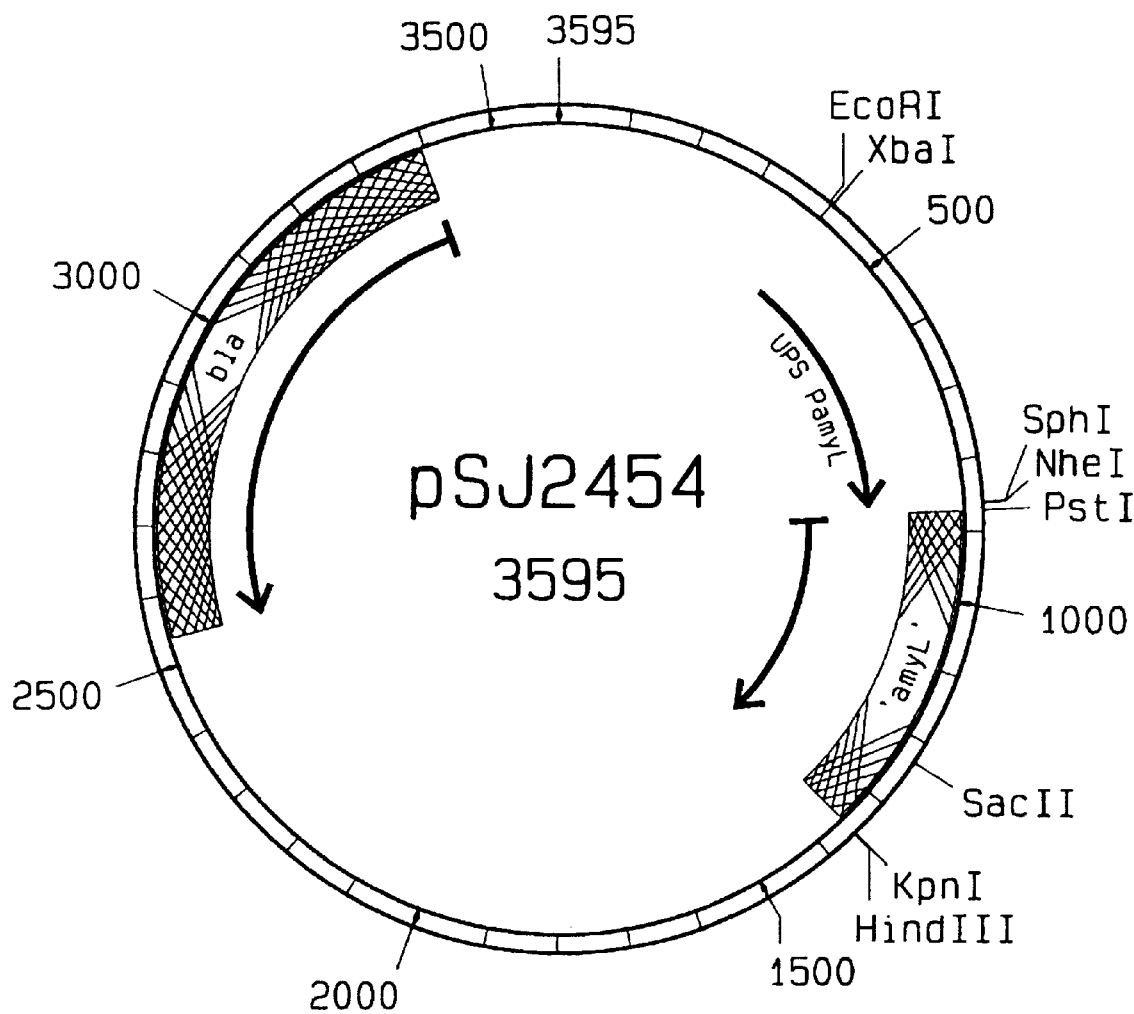
Figure 6:
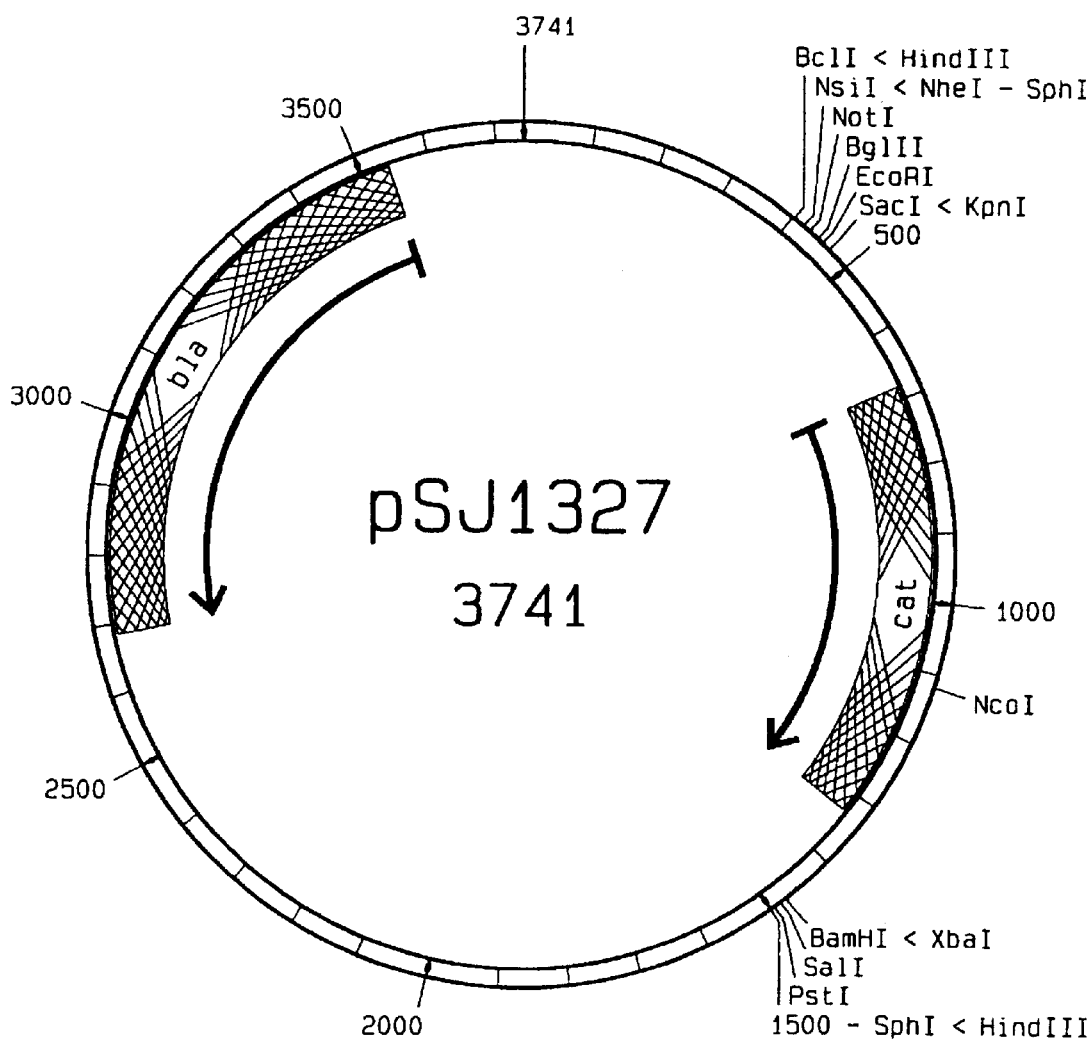
Figure 7:
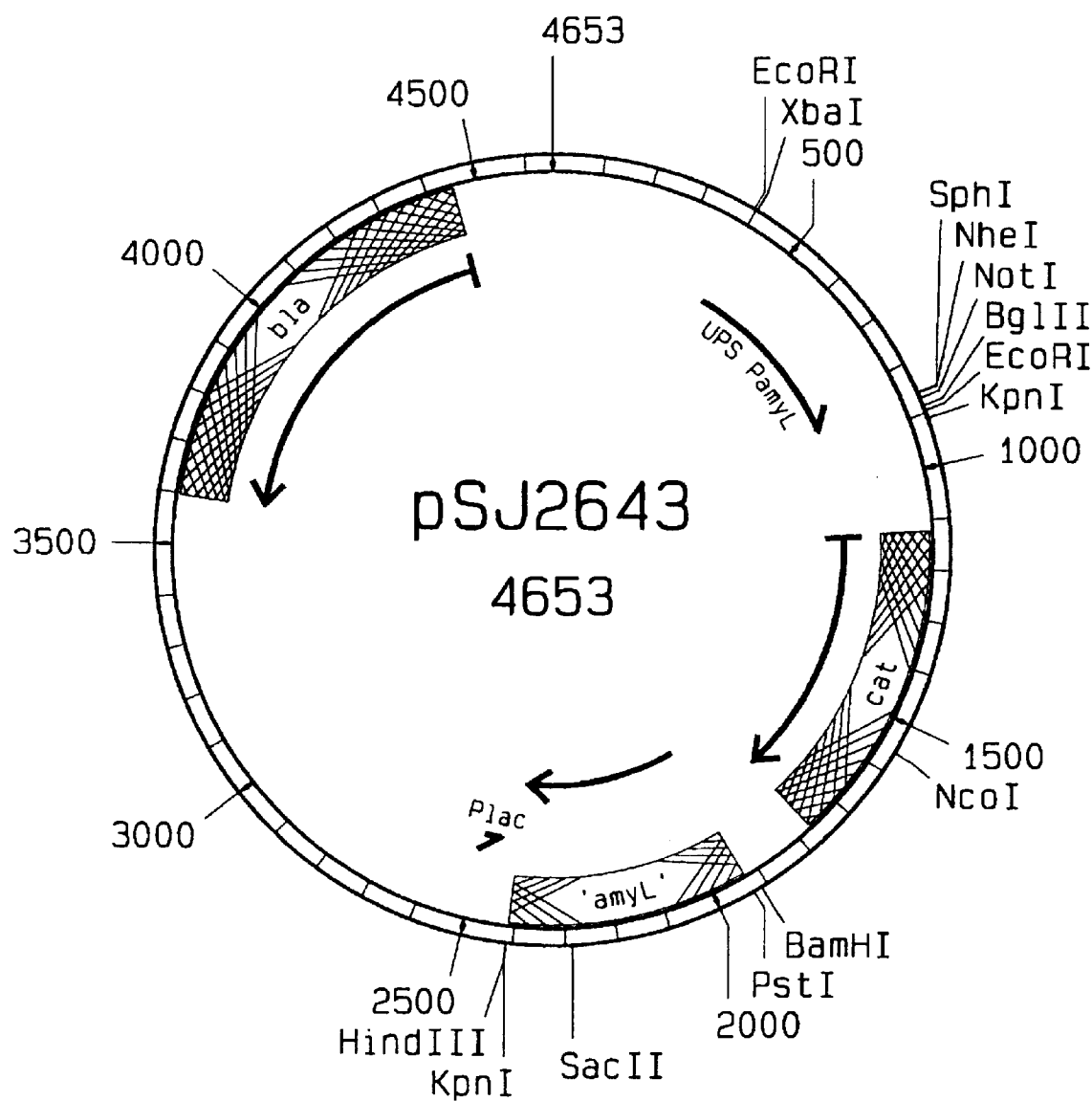
Figure 8:
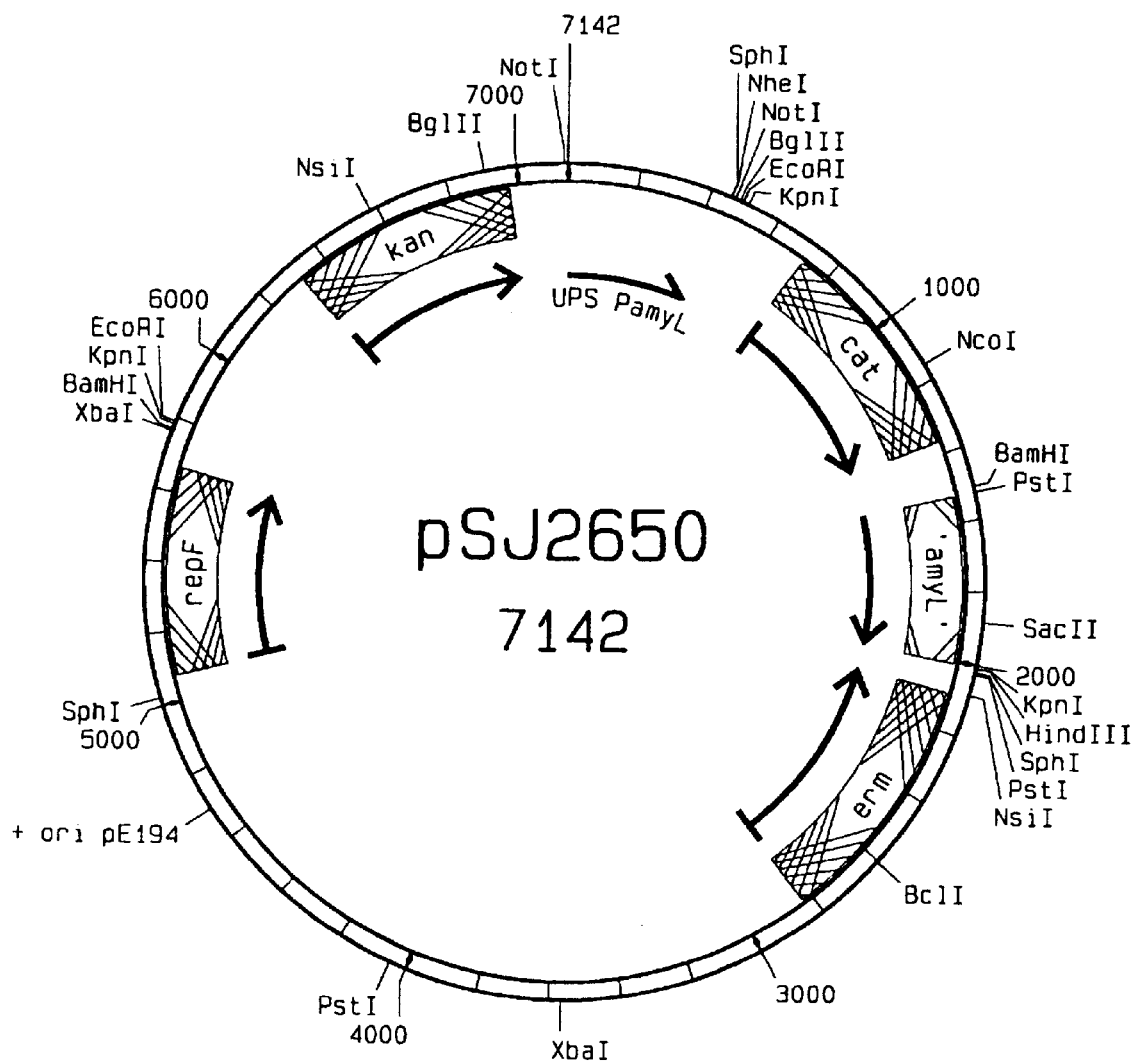
Figure 9:
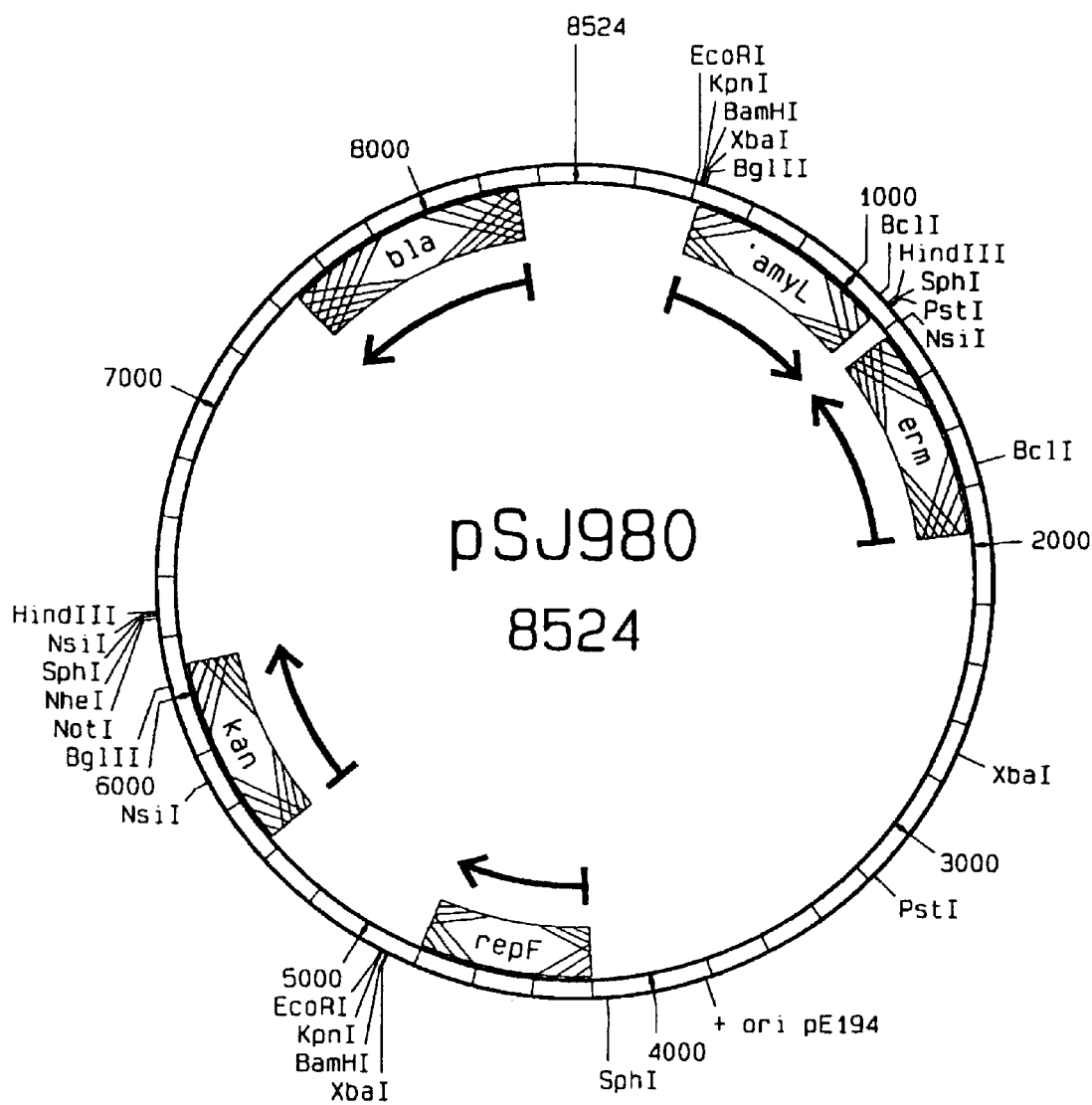

EcoRI  XbaI  <---- amyLV2 18-43 ------>
5'-TGAGTGAATTCTCTAGACCTTCTTTGTGCTTGGAAGCAGAGCC-3'  (SEQ ID NO:2)
``` pSJ2454 (FIG. 5) was derived from pSJ2433 by ligation of a 0.5 kb PstI-KpnI fragment from the α-amylase (amyL) gene on pDN1981 (denoted 'amyL') to PstI+KpnI digested pSJ2433 and transformation of *E. coli* SJ6 (Diderichsen et al., 1990) by electroporation, selecting AmpR, 200 μg/ml.

pSJ1327 (FIG. 6) contains a pC194 (Horinouchi and Weisblum, 1982. (Horinouchi, S., and Weisblum, B. (1982). Nucleotide sequence and functional map of pC194, a plasmid that specifies chloramphenicol resistance. J. Bacteriol., 173, 559–567)) derived cat gene inserted into a polylinker in a pUC19 derivative. The cat gene, which specifies chloramphenicol resistance, was excised from pDN1600 as a 1.0 kb BamHI-BglII fragment, ligated to BamHI digested pDN3000 (Diderichsen et al., 1990), and transformed into *E. coli* SJ6 selecting AmpR (200 μg/ml).

pSJ2643 (FIG. 7) contains the cat gene inserted between the two amyL derived segments in pSJ2454. The cat gene was excised as a 1.1 kb NheI-XbaI fragment from pSJ1327, ligated to NheI digested pSJ2454, and transformed to *E. coli* SJ6 by electroporation, selecting chloramphenicol resistance (CamR, 6 μg/ml), to create pSJ2643. "Plac" indicates the pUC19 derived beta-galactosidase promoter.

pSJ2650 (FIG. 8) contains the UPS_PamyL-cat-'amyL' segment on a temperature-sensitive Bacillus plasmid. pSJ2643 was digested with XbaI+HindIII, the 2.0 kb fragment isolated, ligated to the 5.1 kb NheI-HindIII fragment from pSJ980 (FIG. 9; U.S. Pat. No. 5,698,415), and transformed into *B. subtilis* DN1885 (Diderichsen et al., 1990) competent cells selecting CamR and kanamycin resistance (KanR), 6 μg /ml and 10 μg /ml, respectively, on LBPSG plates (WO 96/23073)), to give pSJ2650. "repF" indicates the pE194-derived replication protein gene, "+ori pE194" indicates the pE194 replication origin, and "erm" indicates the erythromycin resistance gene of pE194. This may also be denoted "ermC".

1B. *B. licheniformis* transformation:

The *B. licheniformis* strain described in example 6 of U.S. Pat. No. 5,698,415, which contains one chromosomal copy of the α-amylase (amyL) gene expressed from a mutant amyL promoter, was used as host strain. pSJ2650 was introduced into this strain by protoplast transformation (Akamatzu and Sekiguchi, 1984 (Akamatsu, T., Sekiguchi, J. (1984). An improved method of protoplast regeneration for Bacillus species and its application to protoplast fusion and transformation. Agric.Biol. Chem., 48, 651–655)), selecting for erythromycin resistance (ErmR, 2 μg/ml) at 30° C. Regenerants were isolated after two weeks incubation. Three strains were kept, SJ3034, SJ3035, and SJ3036.

1C. Chromosomal integration and excision:

Strains SJ3035 and SJ3036 were streaked on plates with 6 μg/ml chloramphenicol and 5 μg/ml erythromycin, and incubated at 50° C. 8 amylase-negative colonies from each strain were checked by PCR amplification using primers LWN4726+LWN3825, and all gave an amplified fragment of the correct size. The amplified fragment extends from the NcoI site within the cat gene to a position in the amyL gene 157 bp downstream from the KpnI site, 1007 basepairs in total. This fragment will only arise if pSJ2650 has integrated via the 'amyL' homology.

```
LWN3825

<-amyLV2 1341-1322->
5'-CTGCTGCGACATCAGGATGG-3'  (SEQ ID NO:3)

LWN4726

<-pDN3060 548-528-->
5'-CATGGACTTCATTTACTGGG-3'  (SEQ ID NO:4)
```

Each colony was taken through two consecutive overnight incubations in 10 ml TY medium (WO 91/09129) without antibiotics at 30° C., plated on plates containing 6 μg/ml chloramphenicol, replica plated after overnight incubation at 30° C. to plates containing 6 μg/ml chloramphenicol plus/minus 5 μg/ml erythromycin, and putative erythromycin sensitive colonies restreaked on the same type of plates.

Three chloramphenicol resistant, erythromycin sensitive strains were isolated:

SJ3047 from SJ3035, colony 1.
SJ3048 from SJ3035, colony 2.
SJ3049 from SJ3036, colony 1.

Integration of the cat gene into the amyL promoter region was confirmed by southern analysis.

A restriction map of the amyL gene region had previously been constructed, revealing the amyL promoter to be situated on a 3.35 kb HindIII fragment and on a 1.9 kb ClaI fragment.

The replacement of the amyL promoter with the cat gene should give a net insertion of 835 basepairs. No additional HindIII or ClaI sites are inserted with the cat gene.

Consequently, chromosomal DNA was extracted from SJ3047-49, digested separately with HindIII and ClaI, separated on agarose gels, transferred by vacuum blotting to immobilon-N membranes, and probed with pSJ1325 (a pUC19 plasmid containing the cat gene) $^{32}$P-labelled by nick-translation.

Hybridization was to a 4.2 kb HindIII fragment in SJ3047 and SJ3048, as expected, but to a somewhat larger fragment in SJ3049. Hybridization was to a 2.7 kb ClaI fragment in SJ3047 and SJ3048, again as expected.

Consequently, strains SJ3047 and SJ3048 which are amylase-negative have the amyL promoter replaced by a cat gene, as desired.

EXAMPLE 2

Isolation of an Improved α-amylase (amyL) Promoter.

2A. Plasmid constructions.

U.S. Pat. No. 5,698,415 claims variant promoters derived from the *B. licheniformis* amyL promoter. With reference to claim 1 in the above patent, such a variant promoter is a fragment of the sequence given in this claim, in which $N^2$–$N^9$ has the sequence ATGTATCA. Such a variant promoter was constructed by incorporating the desired mutation into a long PCR primer (#28902) covering the amyL promoter region. Another PCR primer, LWN3216, reads upstream from a position spanning the PstI site in the AmyL signal peptide coding region. Together, these primers allow PCR amplification of a variant amyL promoter fragment.

```
#28902:

XbaI  SphI  ←----- fragment of sequence
5'-GCTCTAGAGCATGCTGGAAGAAAATATAGGGAAAATGGTA-
   given in claim 1, U.S. Pat. No. 5,698,415
CTTGTTAAAAATTCGGAATATTTATACAATATCATATGTATCAC-
                                    -------→
ATTGAAAGGGGAGGAGAATCATG-3' (SEQ ID NO:5)

LWN3216:

5'-GCTGCTGCAGAATGAGGCAG-3' (SEQ ID NO:6)
```

Figure 10:
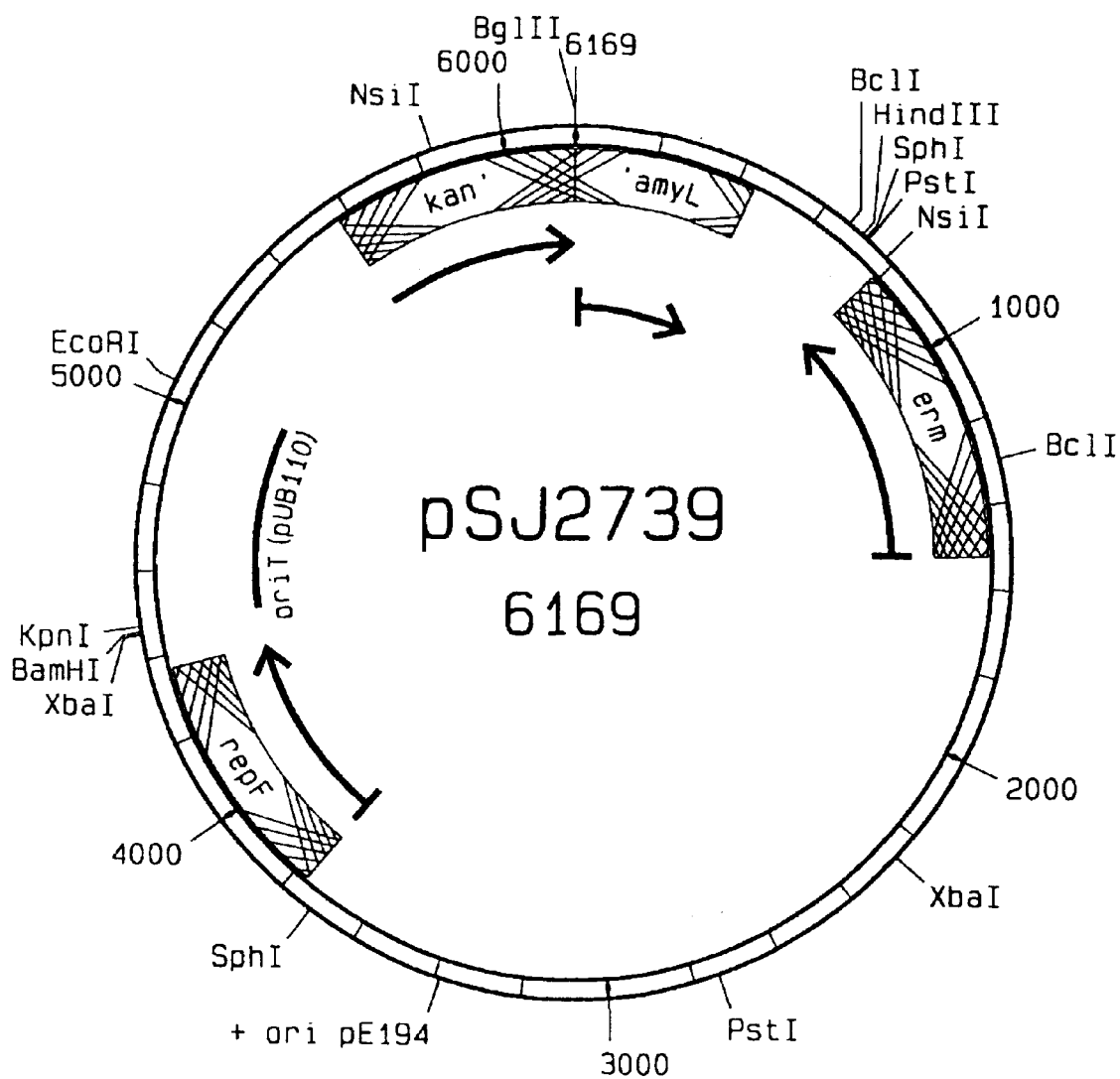
Figure 11:
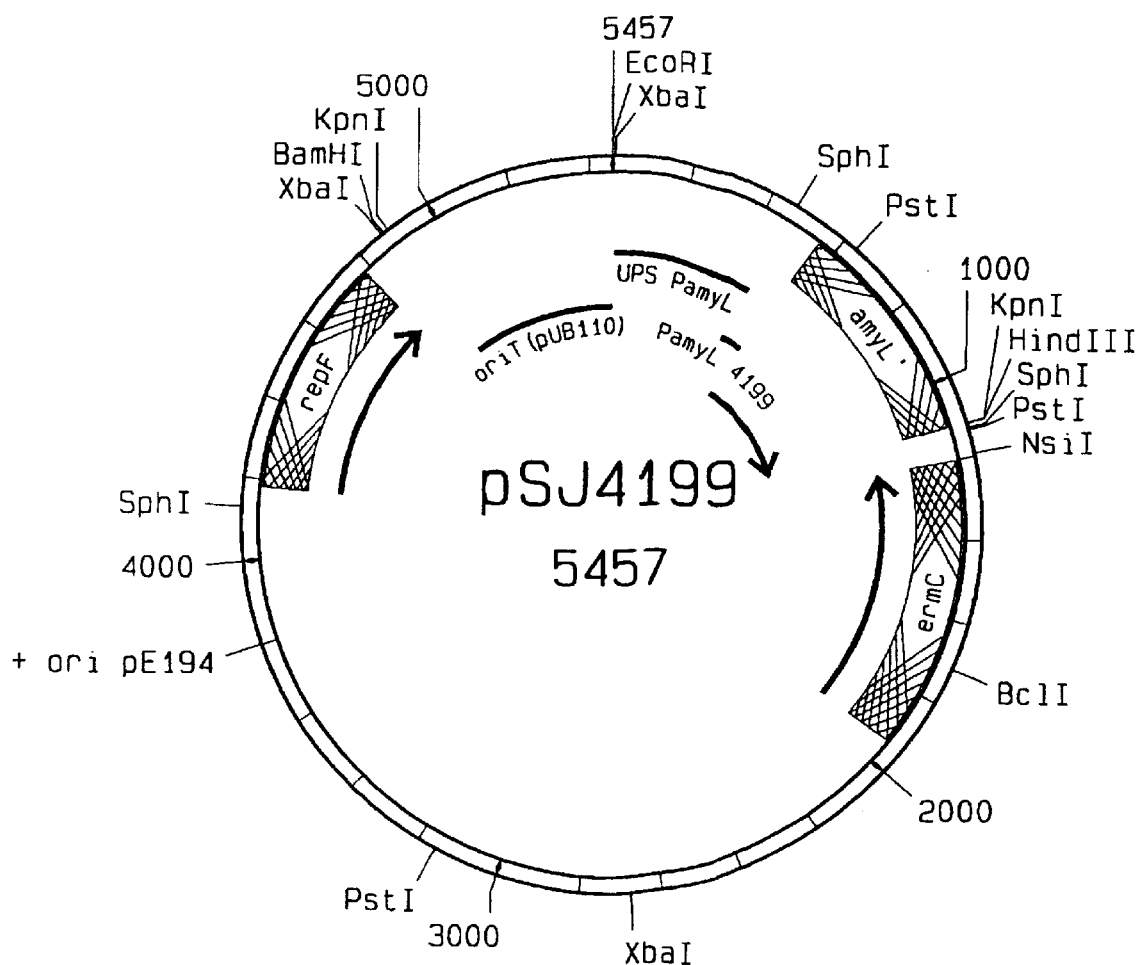

A mobilizable, temperature-sensitive plasmid containing the variant promoter flanked by amyL DNA in a form suitable for integration into the chromosome of strain *B. licheniformis* SJ3047 was constructed as follows:

The substrate for PCR amplifications was pDN1981, which had been digested with BglII. Primer #28902 was used together with primer LWN3216, at an annealing temperature of 45° C. A correctly sized PCR product was obtained, digested with SphI+PstI, ligated to the 3.6 kb SphI-PstI fragment of pSJ2643, the ligation mixture then digested with EcoRI+HindIII, and the 1.1 kb fragment (isolated from a mixture of fragments) ligated to the 4.4 kb EcoRI-HindIII fragment from pSJ2739 (FIG. 10; described in WO 96/23073 "DNA integration by transposition"). The ligation mixture was transformed into competent *B. subtilis* DN1885 selecting erythromycin resistance (5 μg/ml) at 30° C. The recombinant plasmids were analyzed by restriction mapping, and the amyL promoter region on the plasmid designated pSJ4199 (FIG. 11) was DNA sequenced, using primer LWN3207, and found to have the desired sequence. "oriT(pUB110)" denotes the cis acting sequence of pUB110 necessary for conjugative mobilization of the plasmid, see WO 96/23073. "PamyL 4199" denotes the variant amyL promoter.

Figure 12:
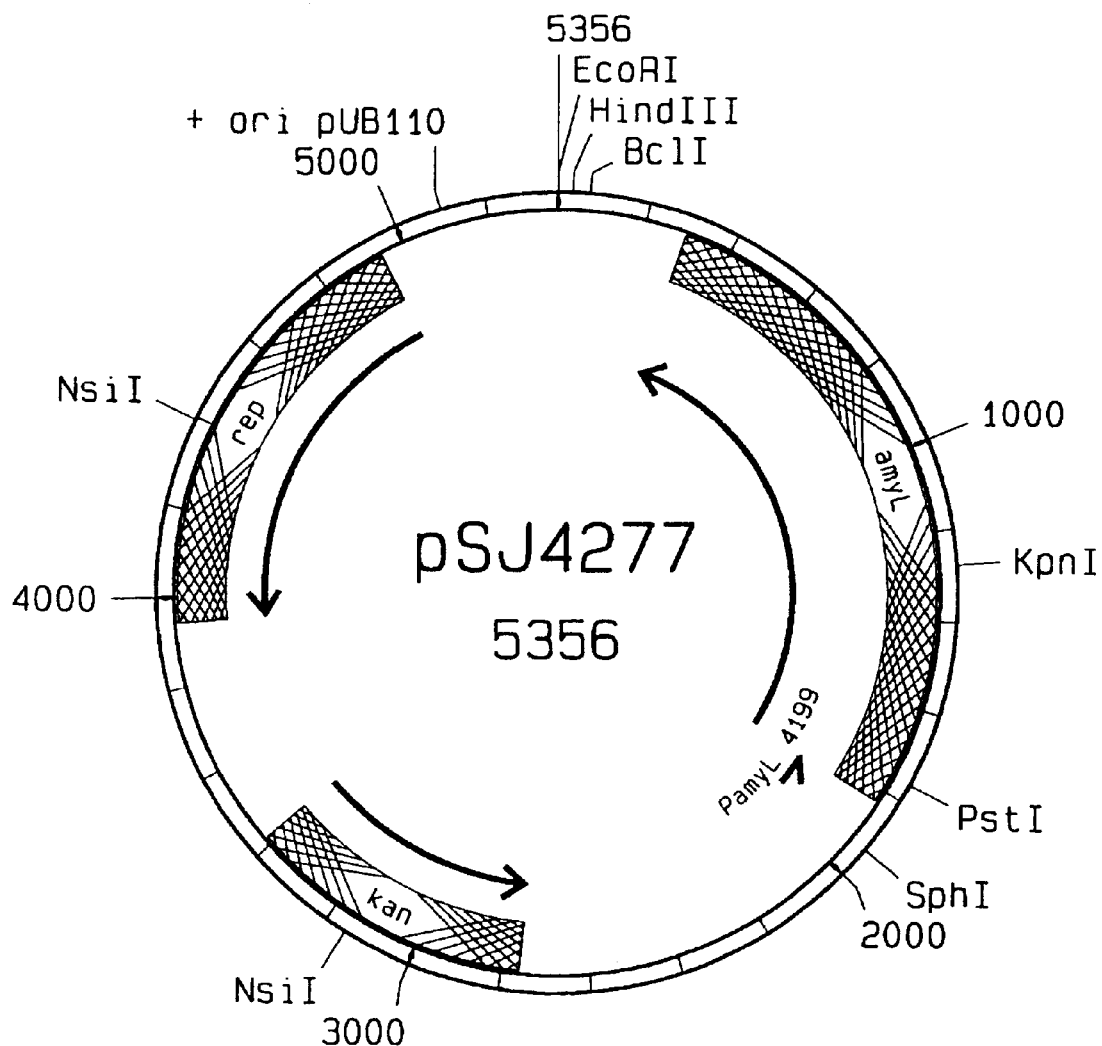

The variant amyL promoter was used to replace the amyL promoter found on plasmid pDN1981. It was excised as a 0.2 kb SphI-PstI fragment from pSJ4199, and ligated to the 5.0 kb SphI-PstI fragment from pDN1981. The ligation mixture was transformed into *B. subtilis* DN1885, selecting kanamycin resistance (10 μg/ml). Two transformants were kept, as SJ4277 (DN1885/pSJ4277; FIG. 12) and SJ4278 (DN1885/pSJ4278). "rep" denotes the pUB110 replication protein gene.

2B. Mobilization into *B. licheniformis* and chromosomal integration.

Plasmid pSJ4199 was transformed into competent cells of *B. subtilis* PP289-5 (dal-, pLS20, pBC16; WO 96/23073, example 4) selecting erythromycin (5 μg/ml) and tetracycline (5 μg/ml) resistance on D-alanine (100 μg/ml) plates at 30° C.

Two transformants were kept, SJ4237 and SJ4238.

Each of these donor strains were used to transfer their plasmid into *B. licheniformis* by conjugation, essentially as described in WO 96/23073, example 11. Transconjugants were almost exclusively tetracycline sensitive.

One transconjugant derived from each donor strain was kept: SJ4258 (from SJ4237) and SJ4259 (from SJ4238), both containing pSJ4199.

These strains were streaked on LBPSG plates supplemented with chloramphenicol (6 μg/ml) and erythromycin (5 μg/ml) at 50° C. overnight. Amylase positive colonies were obtained from each strain, and 4 such colonies from each strain were inoculated in TY medium without antibiotics at 30° C. for 3–4 subsequent transfers, to allow replication, excision, and loss of the plasmid. Amylase positive, erythromycin sensitive colonies were obtained from each transconjugant strain, and kept as SJ4270 (from SJ4258) and SJ4271 (from SJ4259).

2C. Test of variant promoter strain.

The efficiency of the variant promoter was tested in shake flask experiments, in which α-amylase production from each of the integrant strains was compared to α-amylase production from the control strain (the strain, from which SJ3047 was derived by deletion of the promoter). Incubation was in duplicate in BPX medium (EP 0 506 780), for 7 days at 37° C., and α-amylase activity measured at day 2, 5 and 7.

The activity is given relative to the highest activity measured from the control strain.

| Strain | Day 2 yield | Day 5 yield | Day 7 yield |
|---|---|---|---|
| control (1) | 8.5 | 57 | 90.5 |
| control (2) | 9.5 | 65 | 100 |
| SJ4270 (1) | 13.5 | 106.5 | 170.5 |
| SJ4270 (2) | 14 | 89.5 | 155 |
| SJ4271 (1) | 12.5 | 90.5 | 174 |
| SJ4271 (2) | 14 | 89.5 | 170 |

The variant promoter present in strains SJ4270 and SJ4271 is clearly improved with respect to α-amylase production, relative to the promoter of the control strain.

EXAMPLE 3

Construction of a Strain Containing two Divergently Transcribed Expression Cassettes 3A. Plasmid constructions:

A plasmid was designed, in which an entire copy of the amyL gene was inserted between the UPS_PamyL segment and the PamyL_4199 promoter on pSJ4199, so that the two amyL promoters on the resulting plasmid would read in opposite directions.

Figure 13:
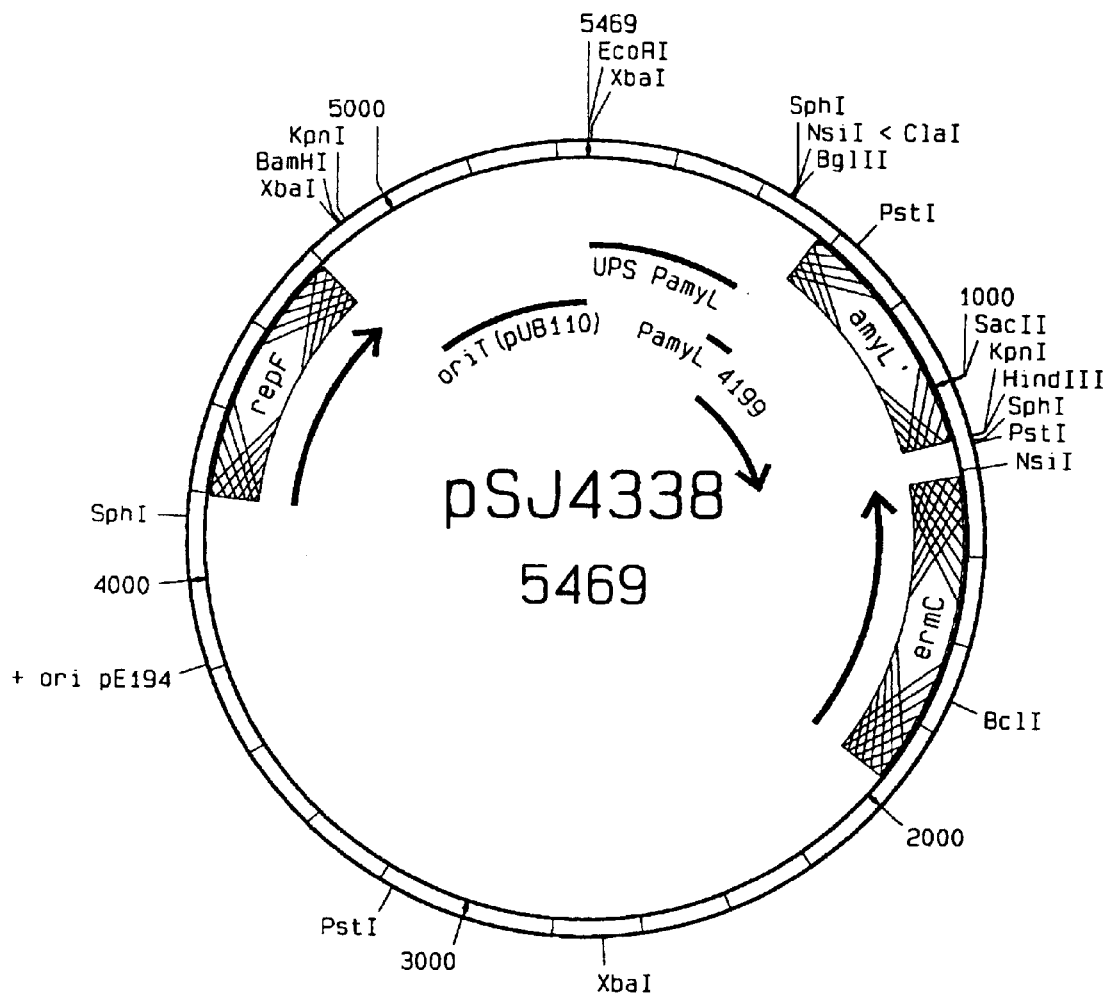

Plasmids pSJ4338 (FIG. 13) and pSJ4339 were constructed. These are almost identical to the integration plasmid pSJ4199, except for a few extra restriction sites introduced between the UPS_PamyL and PamyL_4199 segments. Plasmid pSJ4278 was used as template in a PCR amplification with primers #113123 and LWN3216.

```
#113123:

SphI    ClaI    BglII
5'-GTCAGCATGCATCGATAGATCTTGGAAGAAAATATAGGG-3'  (SEQ ID NO:7)

LWN3216:

5'-GCTGCTGCAGAATGAGGCAG-3'  (SEQ ID NO:8)
```

An amplified fragment of 0.19 kb was obtained, purified, and digested with SphI+PstI. It was ligated to the 3.5 kb SphI-PstI fragment of pSJ2643, the ligation mixture digested with EcoRI+HindIII, the fragment of 1.13 kb purified, and ligated to EcoRI+HindIII digested pSJ2739. This ligation mixture was then transformed into competent DN1885 selecting erythromycin resistance (5 μg/ml) at 30° C. Three transformants were obtained. Strain SJ 4338 (DN1885/pSJ4338) contained a plasmid, which was correct as seen by restriction analysis, and the amyL promoter region was found to be correct by DNA sequencing.

Figure 14:
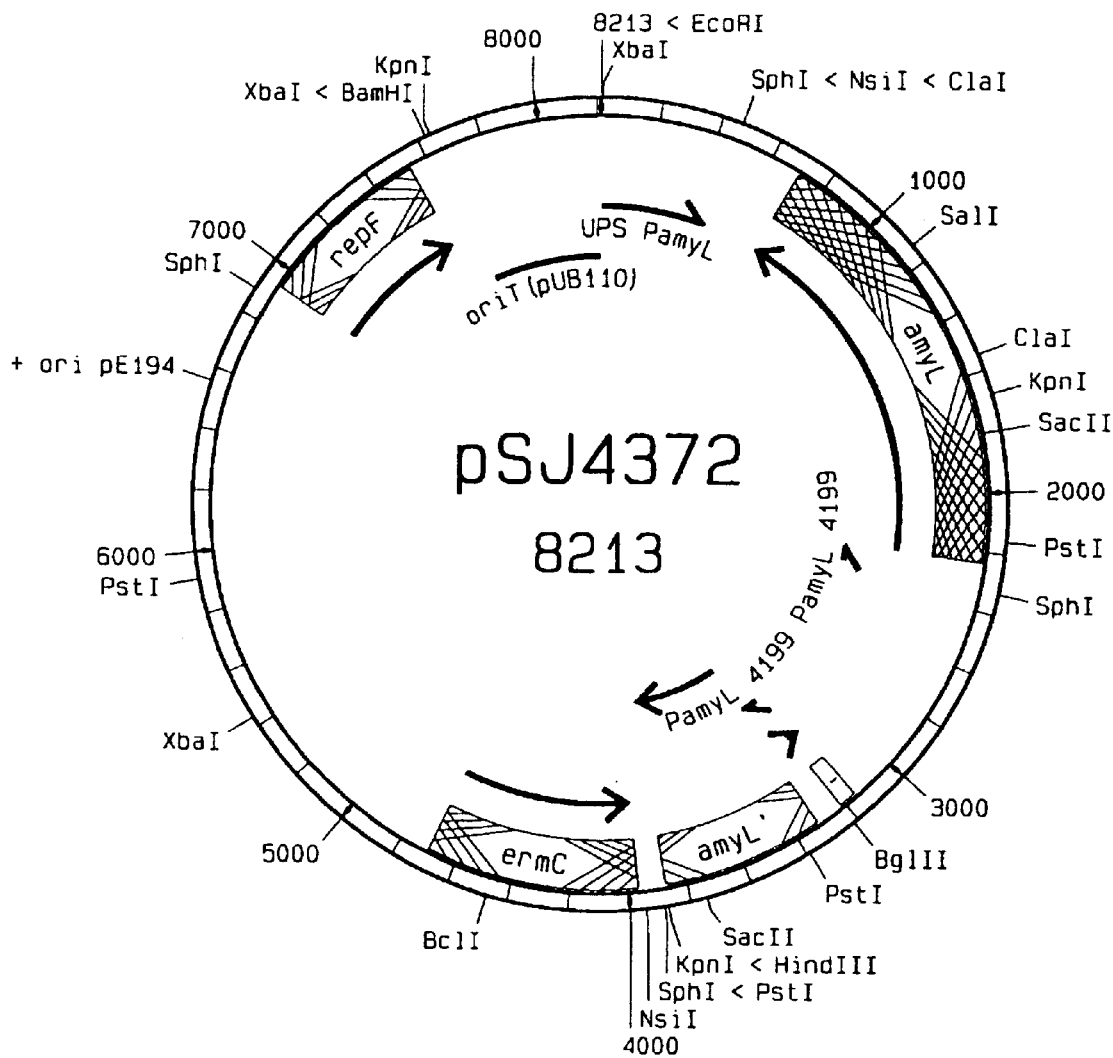

Plasmids pSJ4372 and pSJ4373 (FIG. 14) were then constructed by insertion of the entire amyL gene into the above integration plasmid. Thus, pSJ4277 was digested with BclI+BglII (+with NcoI, to further digest the unwanted fragment) and the 2.8 kb fragment purified. This was ligated to BglII digested pSJ4338, and the ligation mixture transformed into competent DN1885 selecting erythromycin resistance (5 μg/ml) at 30° C. Amylase positive transformants, deemed correct by restriction analysis, were SJ4372 (DN1885/pSJ4372) and SJ4373 (DN1885/pSJ4373).

3B. Transfer to *B. licheniformis* and chromosomal integration:

These plasmids were subsequently transformed into conjugative donor strain host PP289-5, resulting in strains SJ4378 and SJ4379 (both PP289-5/pSJ4373; $Erm^R$ $Tet^R$ $Dal^-$).

Plasmid pSJ4373 was transferred into *B. licheniformis* SJ3047 by conjugation as previously described.

Transconjugants (4 using SJ4378 donor, 9 using SJ4379 donor) appeared after two days.

4 strains were kept: SJ4395 and SJ4396 from SJ4378 donor, SJ4397 and SJ4398 from SJ4379 donor.

The strains were streaked on LBPSG plates with erythromycin (5 μg/ml) at 50° C., and 10 single colonies from each strain then inoculated into 10 ml TY cultures and propagated at 30° C. overnight. Cultures were then spread to single colonies on LBPSG plates, these plates incubated overnight at 30° C., replica plated to LBPSG plates with erythromycin (5 μg/ml), and erythromycin resistance and amylase phenotype scored after overnight incubation. Most colonies were erythromycin sensitive, but amylase negative. From one culture, however, was an erythromycin sensitive, amylase positive strain isolated. This was kept as SJ4414.

3C. Test of two-copy strain:

The performance, in BPX shake flasks, of two-copy strain SJ4414 was compared to that of SJ4270 (the corresponding one-copy strain) in two separate experiments.

BPX shake flasks were incubated for 7 days at 37° C., no antibiotics added, and α-amylase activity measured. For each experiment, activities given are relative to the activity obtained from the one-copy strain.

| | Experiment A | |
|---|---|---|
| Strain | Yield | pH of spent broth |
| SJ4270 | 100 | 8.0 |
| SJ4414 | 153 | 7.5 |

| | Experiment B | |
|---|---|---|
| Strain | Yield | pH of spent broth |
| SJ4270 (1) | 100 | 8.5 |
| SJ4414 (1) | 126 | 8.0 |

Experiments A and B clearly demonstrate that the two-copy strain SJ4414 gave a higher yield as compared to the corresponding one-copy strain SJ4270.

Further, SJ4414 samples were spread on LBPSG. All single colonies (about 30, from each flask, including those with low pH) were amylase-positive, indicating the stable maintenance of the two integrated copies.

EXAMPLE 4

Chromosomal Gene Insertion in Two Successive Steps

Figure 15:
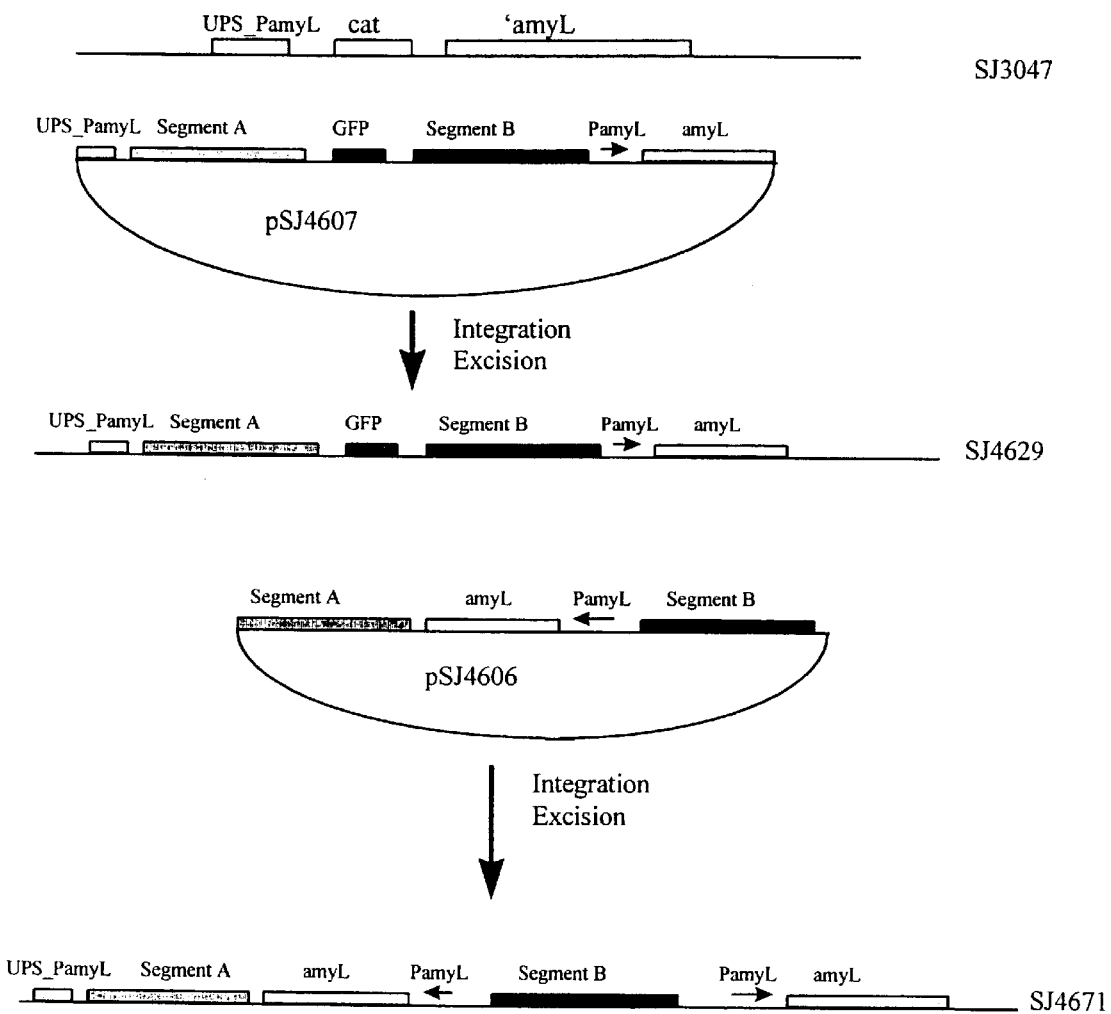

As an alternative to the construction pathway described above (example 3) a temperature sensitive, mobilizable vector pair was designed and constructed to allow for easy cloning and integration of any expression cassette. The first vector contains two regions with homology to neighbouring segments of the host cell chromosome. In between, it contains a multilinker site and a large (e.g. 5 kb) segment of "neutral" DNA. The second vector contains only the large segment of "neutral" DNA, but has the multilinker site inserted in the middle of this segment, and in the opposite relative orientation as compared to the first vector. The vectors and the strategy behind their use is illustrated in the schematic drawing in FIG. 15. In addition to the previously defined notation, "segment A" denotes one half of the large "neutral" DNA segment, "segment b" denotes the other half of this segment, and "GFP" denotes a gene expressing Green Fluorescent Protein.

As "neutral" DNA suitable for incorporation into production strains was chosen a composite of two segments from the *Bacillus subtilis* 168 pps gene region (Accession Number Z34883 in Gen-Bank/EMBL), taken from strain SJ2692 which is the *B. subtilis* strain used in the international genome sequencing programme. One segment is entirely internal in gene pps2, the other segment entirely internal in pps4. They were chosen because they contained very few restriction enzyme sites, and because they, as cloned, would not be expected to encode any gene products.

Figure 16:
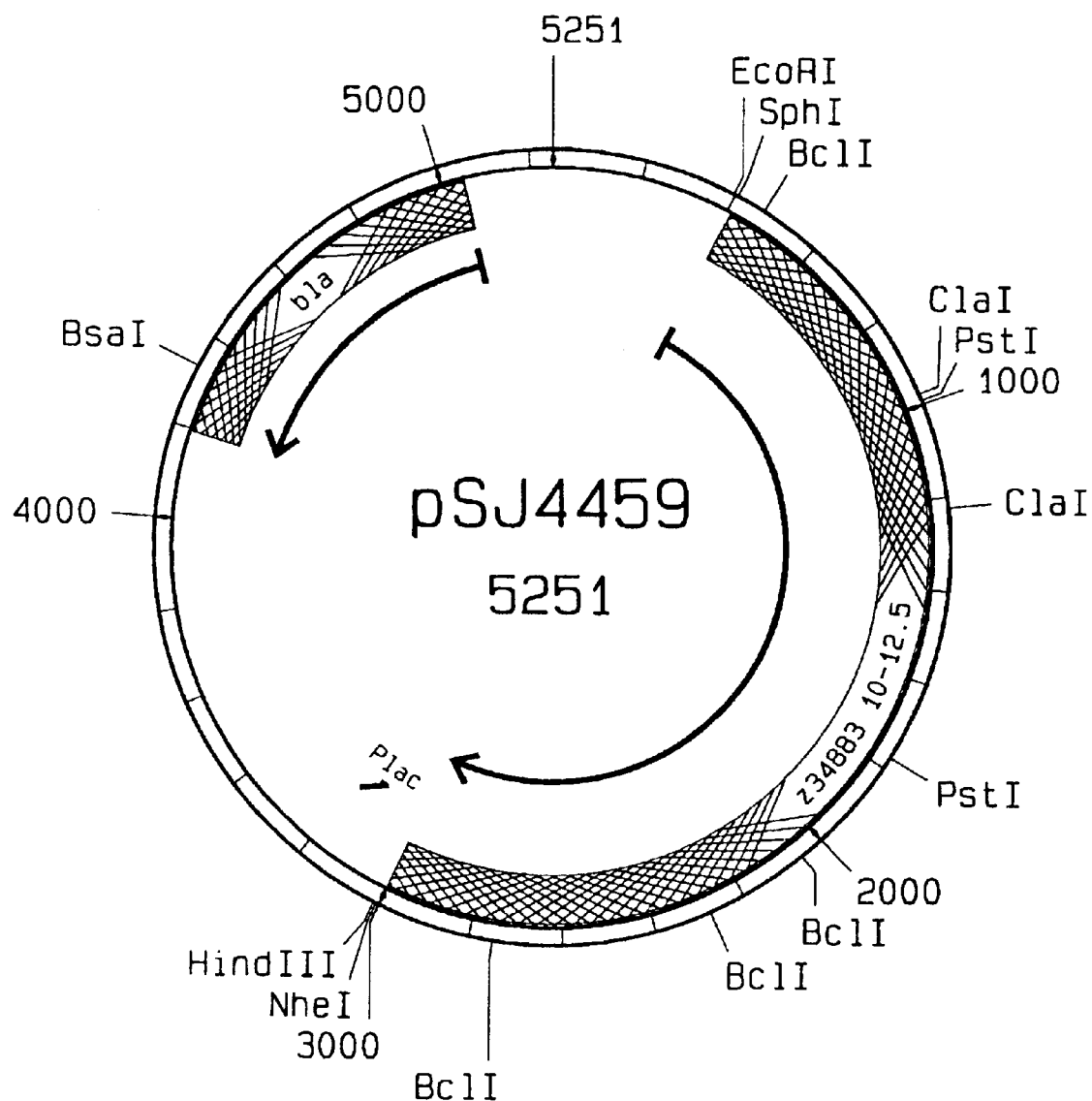

4A. Construction of vector for integration of first expression cassette copy:

Plasmid pSJ4459 (FIG. 16) was constructed as follows:
Chromosomal DNA from SJ2692 was PCR amplified with primers #119882 and #119883.

```
#119882:

EcoRI  SphI<-  z34883 9964-9987---->
5'-CAGTGAATTCGCATGCAGCAGGTAGTTCTATCAAACCG-3'  (SEQ ID NO:9)

#119883:

HindIII NheI<-  z34883 12565-12540-->
5'-GACTAAGCTTGCTAGCCGCTGGATGTTAATGGCATCTGGC-3'  (SEQ ID NO:10)
```

The amplified 2.6 kb fragment was digested with EcoRI and Hin-dIII, and ligated to EcoRI+HindIII digested pUC19. The ligation mixture was transformed, by electroporation, into *E. coli* SJ2 selecting ampicillin resistance (200 μg/ml) on IPTG X-gal plates. Four white colonies were picked for plasmid preparation. All were correct, and could be digested with enzymes EcoRI, Hin-dIII, SphI and NheI. One strain was kept as SJ4459 (SJ2/pSJ4459). "z34883 10–12.5" denotes the amplified fragment from pps2.

Figure 17:
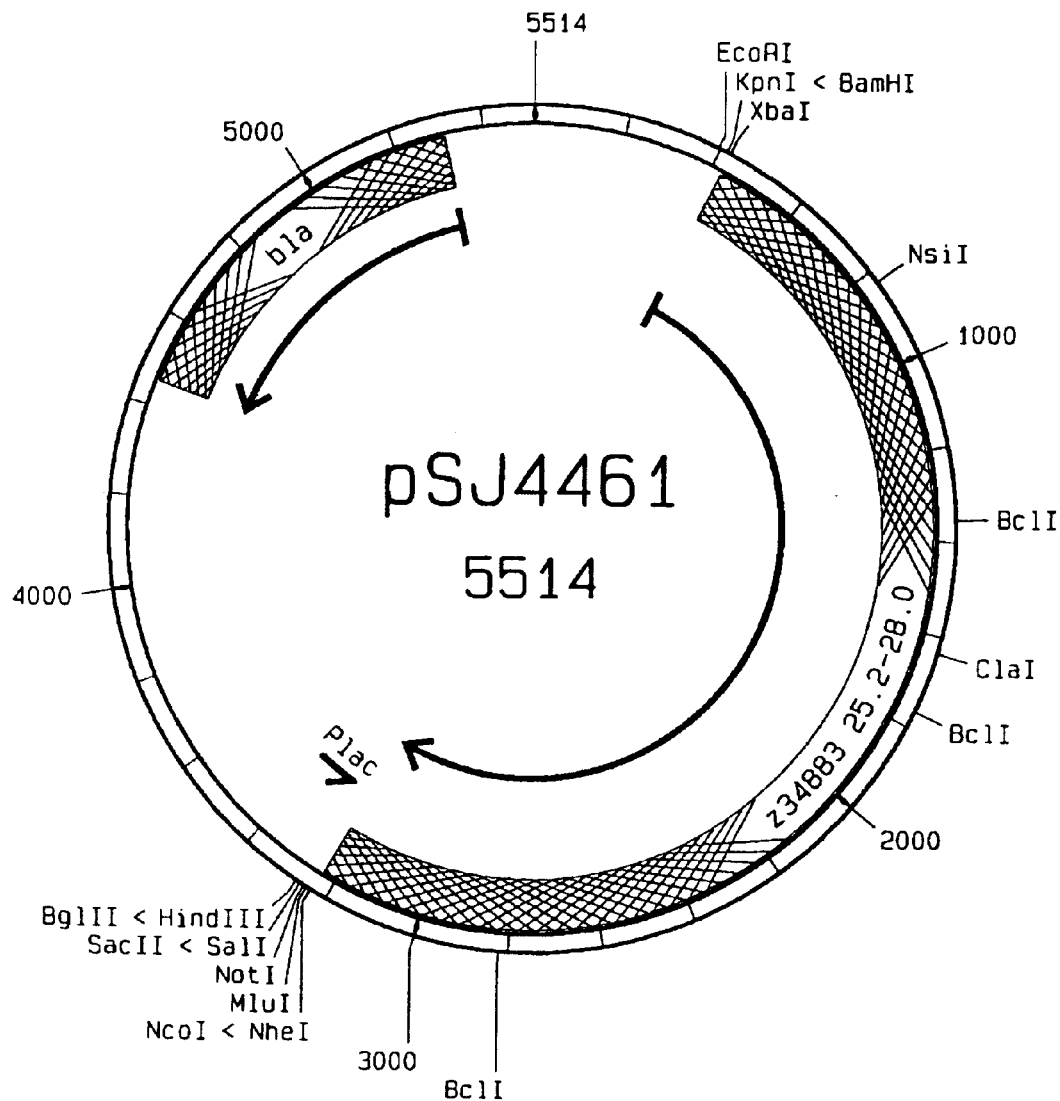

Plasmid pSJ4461 (FIG. 17) was constructed as follows:
Chromosomal DNA from SJ2692 was PCR amplified with primers #119884 and #119885.

```
#119884:

XbaI <-  z34883 25234–25260 ---->
5'-CAGTTCTAGACTTTTACAATAGAAGGAAAAGTCACCC-5'  (SEQ ID NO:11)

#119885:

HindIII BglII SalI SacII NotI   MluI  NheI NcoI
5'-GACTAAGCTTAGATCTGAGCTCCGCGGCGGCCGCACGCGTGCTAGCCATGG <- z34883 28038–28015 ->
    -CCTCTAACAGATTTCGAGGGGCAG-3'  (SEQ ID NO:12)
```

The amplified 2.8 kb fragment was digested with EcoRI and Hin-dIII, and ligated to EcoRI+HindIII digested pUC19. The ligation mixture was transformed, by electroporation, into *E. coli* SJ2 selecting ampicillin resistance (200 μg/ml) on IPTG X-gal plates. Four white colonies were picked for plasmid preparation. Three were correct, and could be digested with enzymes HindIII, XbaI, BglII, SalI, SacII, NotI, MluI, NheI, NcoI. One transformant was kept as SJ4461 (SJ2/pSJ4461). "z34883 25.2–28.0" denotes the amplified fragment from pps4.

Figure 18:
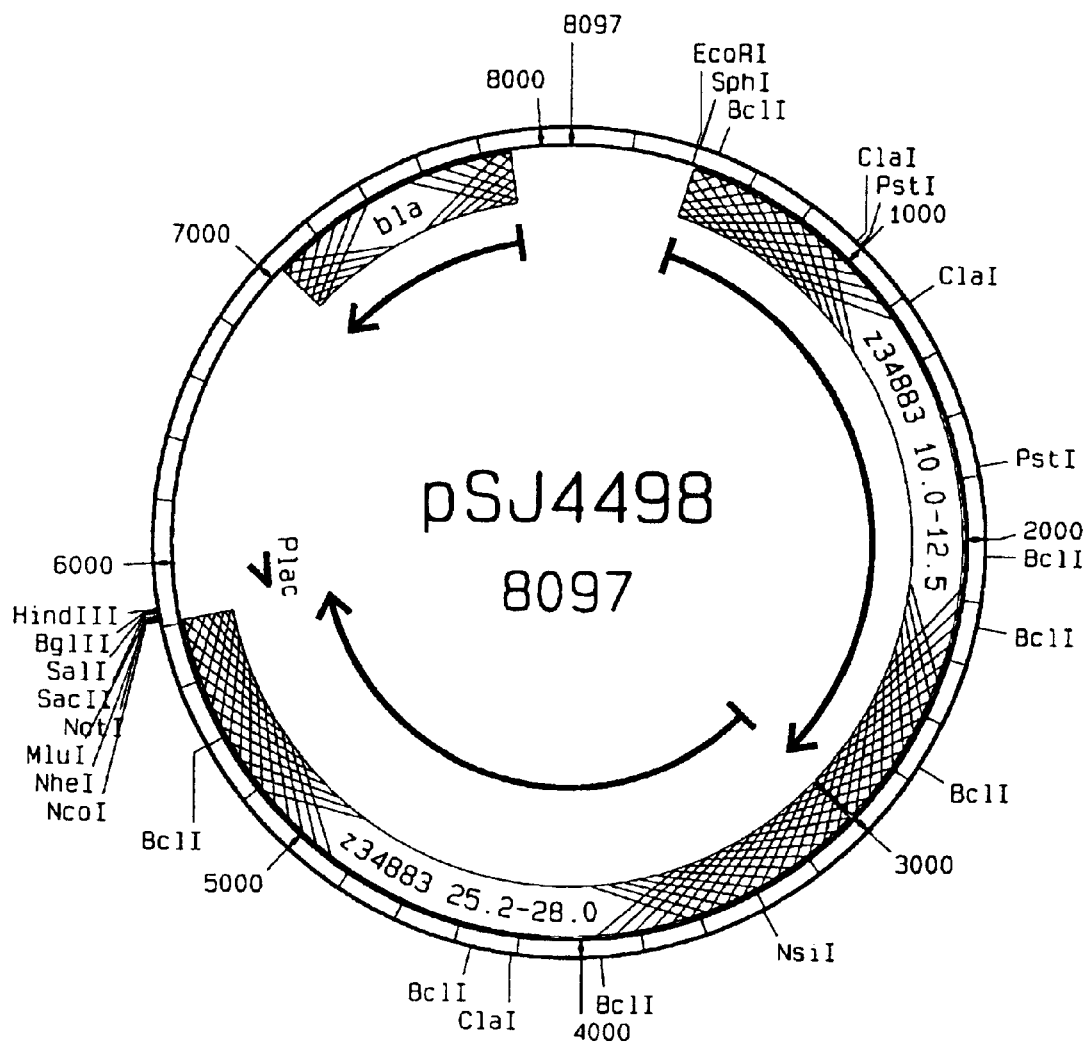

Plasmid pSJ4498 (FIG. 18) was constructed as follows:
Plasmid pSJ4459 was digested with EcoRI+NheI (+ with BsaI to further digest the unwanted part) and the 2.6 kb EcoRI-NheI fragment purified from an agarose gel. The fragment was ligated to EcoRI+XbaI digested pSJ4461, and the ligation mixture transformed (electroporation) into *E. coli* SJ6 selecting ampicillin resistance (6 μg/ml). One strain was kept as SJ4498 (SJ6/pSJ4498).

Figure 19:
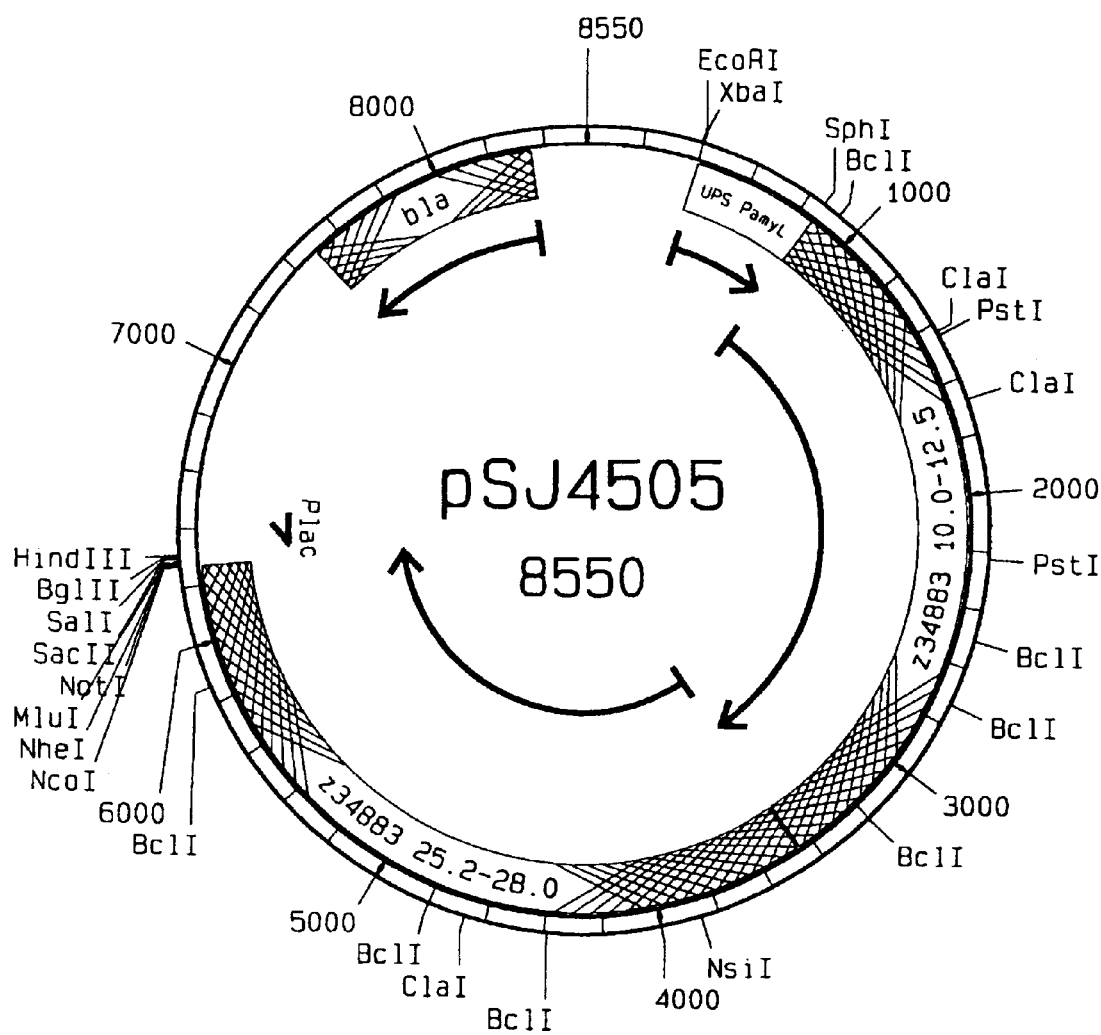

Plasmid pSJ4505 (FIG. 19) was constructed as follows:
pSJ4498 was digested with SphI and HindIII, and the 5.4 kb fragment gel purified. This was ligated to the 3.2 kb SphI-HindIII fragment purified from pSJ2643 (described above, FIG. 7), and the ligation mixture transformed (electroporation) into *E. coli* SJ6 selecting ampicillin resistance (6 μg/ml). One transformant was kept as SJ4505 (SJ6/pSJ4505).

Figure 20:
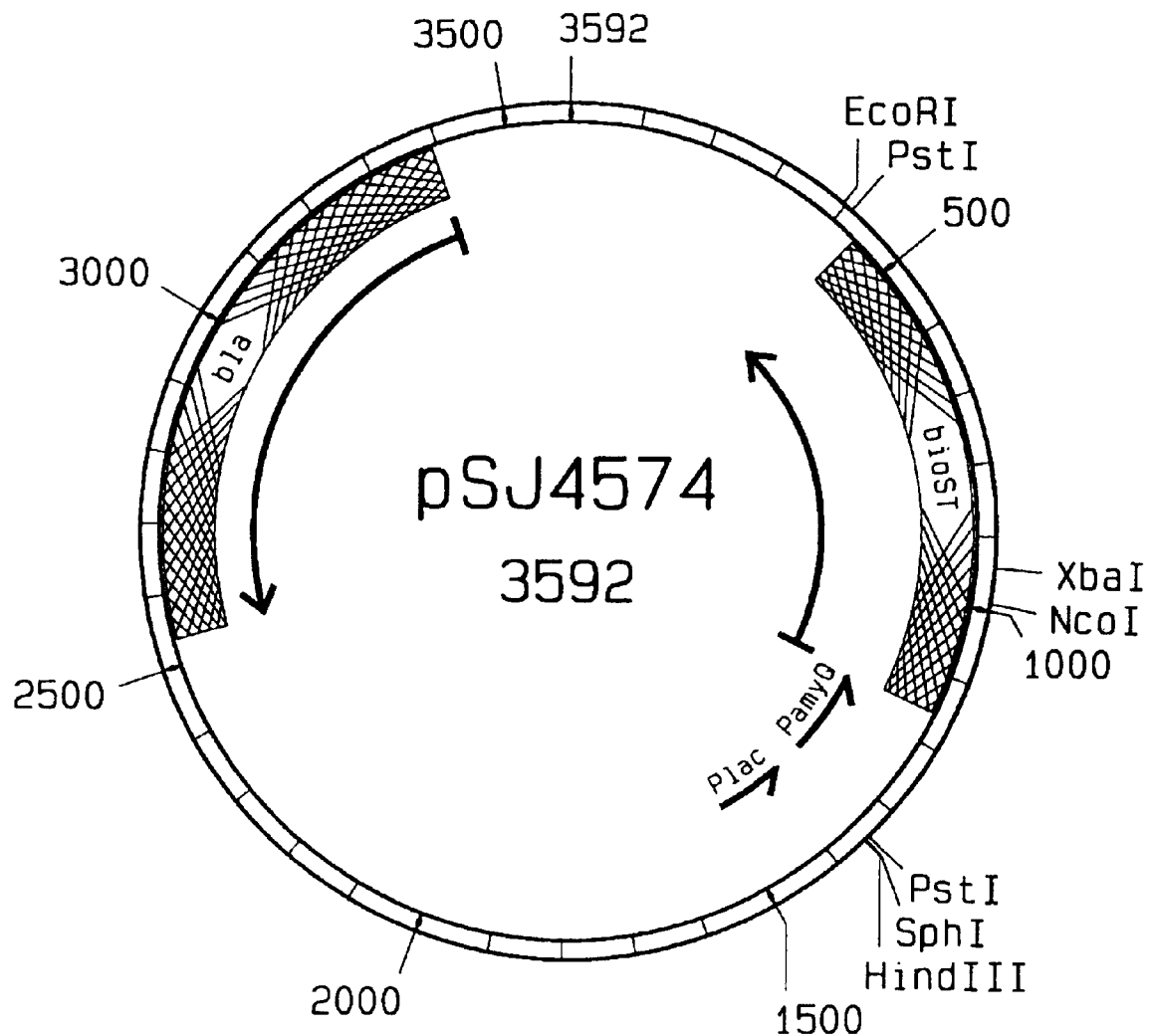

In order to allow visual screening for insertion of the second gene copy, a gene encoding green fluorescent protein was inserted between the two pps gene segments in the first integration vector. The first insertion of the gene of interest using this system would then render the cells GFP positive, whereas the correct insertion of the second copy of the gene of interest would render the cells GFP negative again. A plasmid expressing green fluorescent protein is pSJ4574 (FIG. 20), described in EXAMPLE 1 and FIG. 3 in patent application DK 0792/97; and WO 99/01562. "bioST" denotes the GFP gene, and "PamyQ" the promoter from the *Bacillus amyloliquefaciens* alpha -amylase gene.

Figure 21:
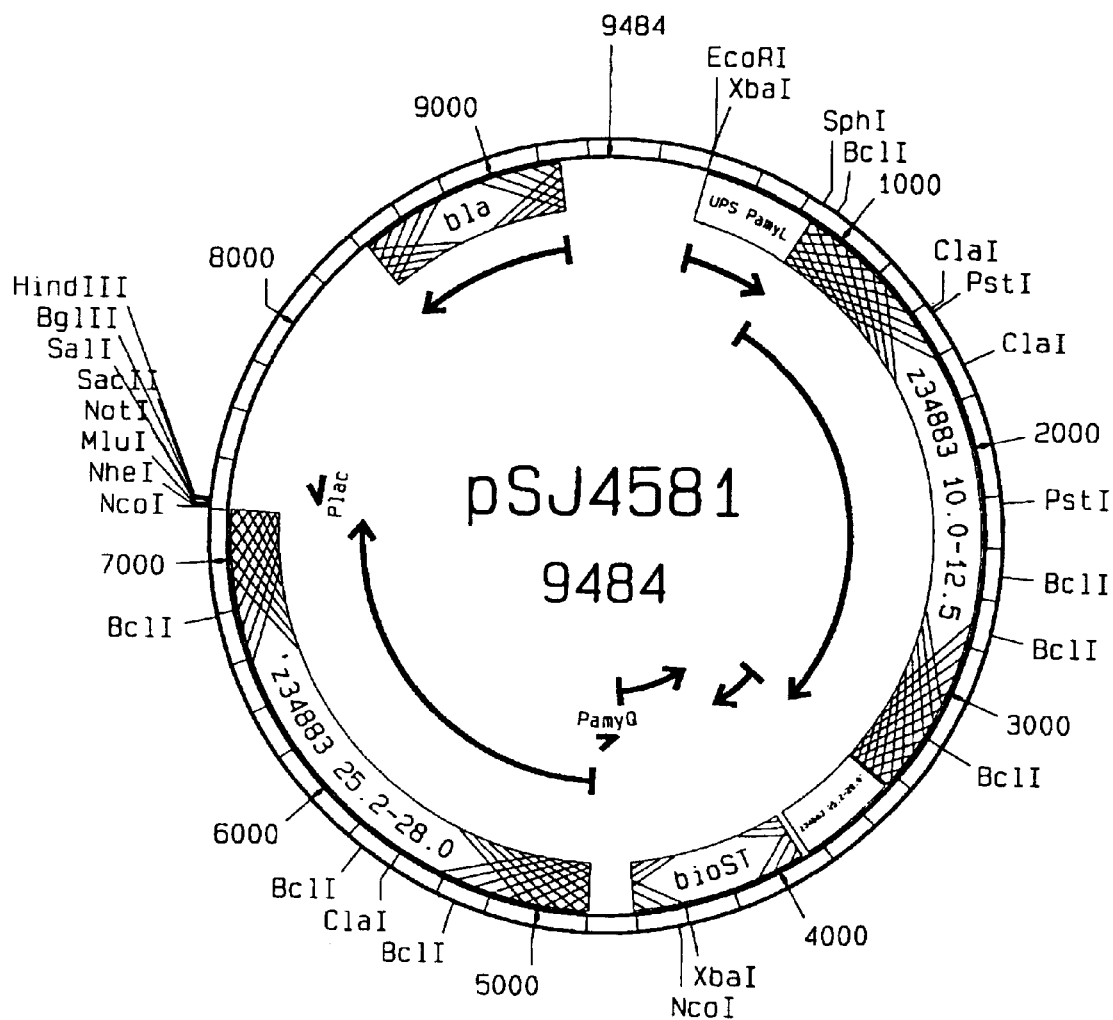

Plasmid pSJ4581 (FIG. 21) was constructed as follows:
pSJ4574 was digested with PstI, and the 0.95 kb fragment gel purified. This fragment was ligated to NsiI digested pSJ450S, and the ligation mixture transformed (electroporation) into *E. coli* SJ2 selecting ampicilin resistance (200 μg/ml). One transformant was kept as SJ4581 (SJ2/pSJ4581).

Figure 22:
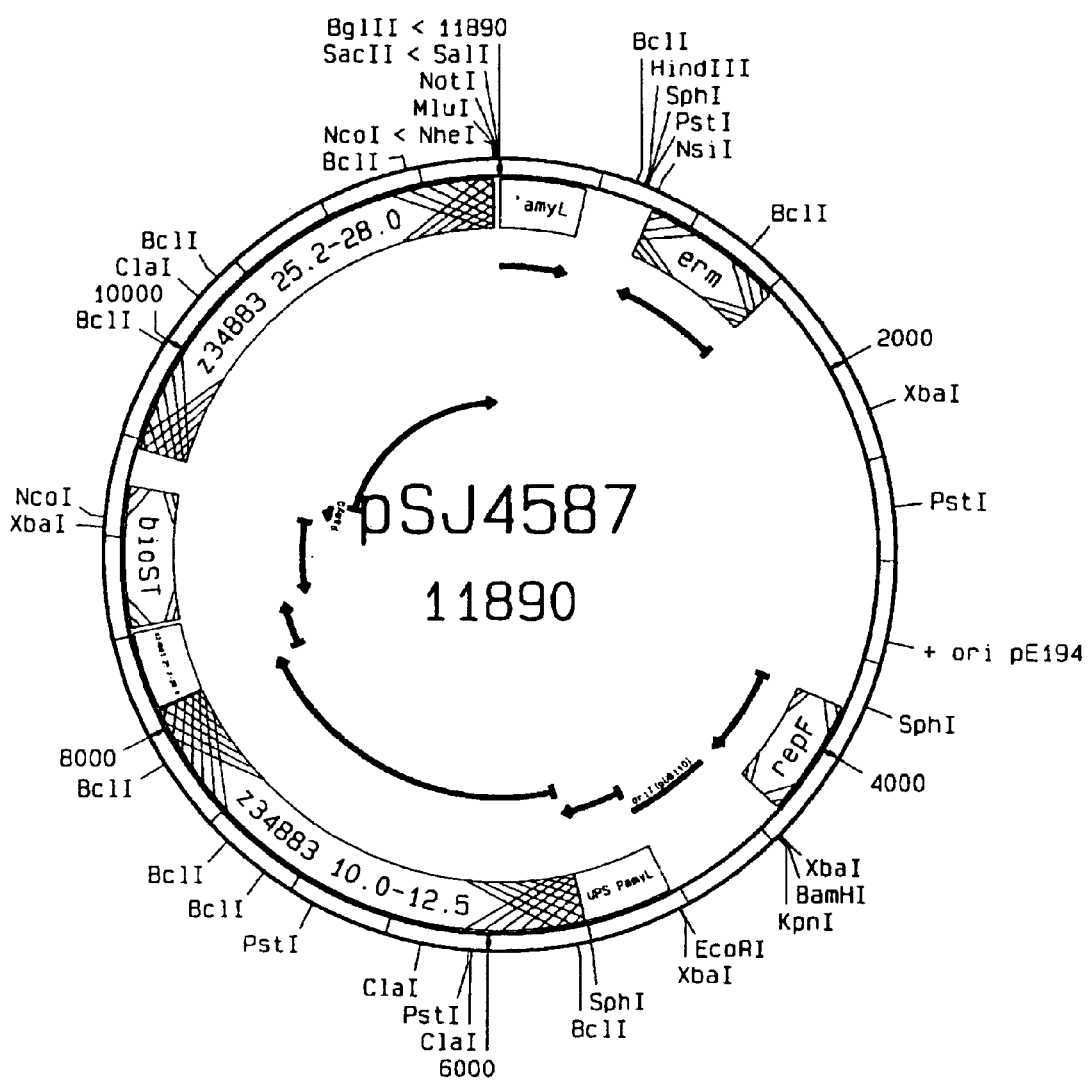

Plasmid pSJ4587 (FIG. 22) was constructed as follows:
pSJ4581 was digested with EcoRI+BglII, and the 6.9 kb fragment gel purified. This fragment was ligated to the 5.0 kb EcoRI-BglII fragment from pSJ2739 (described above, FIG. 10), and the ligation mixture was transformed into *B. subtilis* DN1885 competent cells selecting erythromycin resistance (5 μg/ml) at 30° C. One transformant was kept as SJ4587 (DN1885/pSJ4587).

Figure 23:
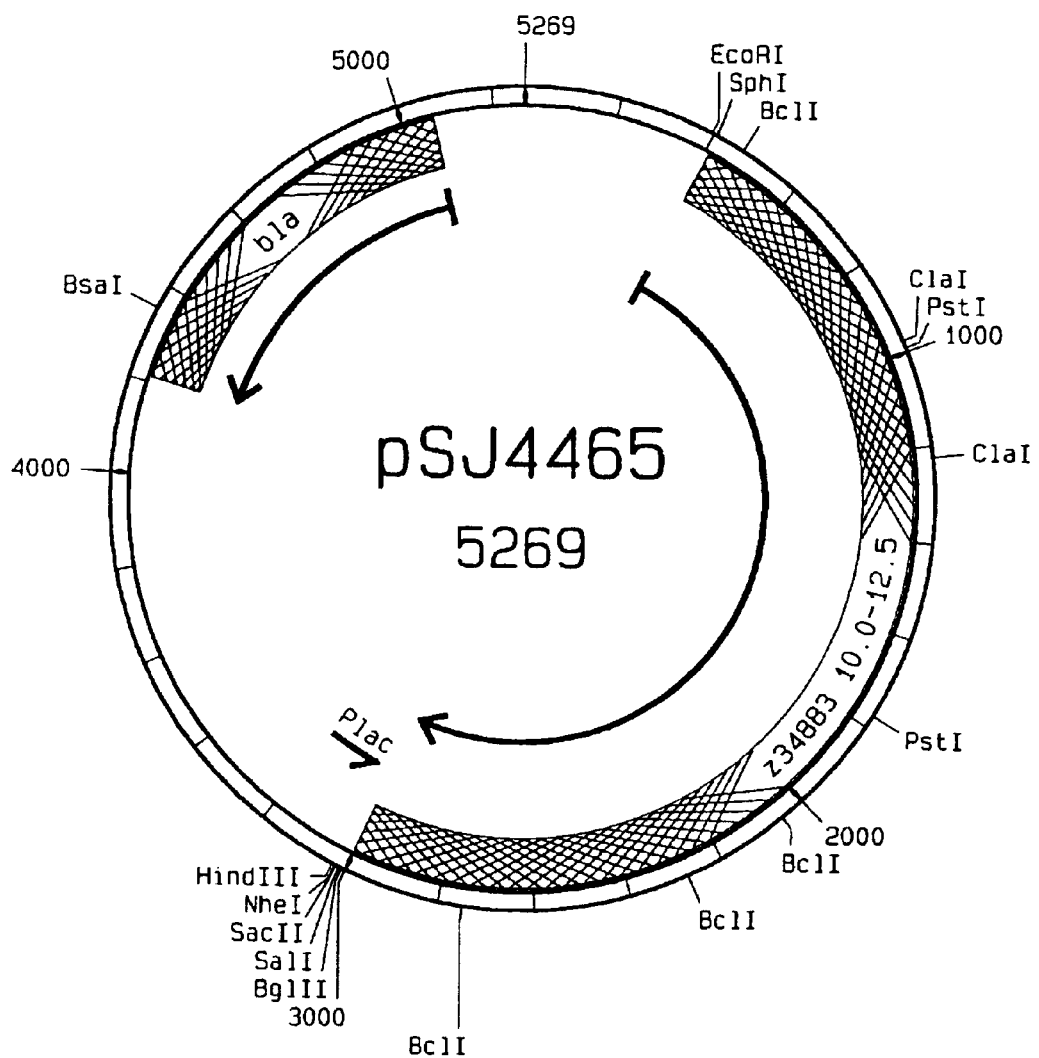

4B. Construction of vector for integration of second expression cassette copy:

Plasmid pSJ4465 (FIG. 23) was constructed as follows:
Plasmid pSJ4459 was used as a substrate in a PCR reaction with primers #119882 and #119886, using 60° C. as annealing temperature and only 10 amplification cycles.
119882: see above

119886:

```
         HindIII NheISacII SalI BglII<- z34883 12565-12540 --->
5'-GACTAAGCTTGCTAGCCGCGGAGCTCAGATCTGCCGCTGGATGTTAATGGCATCTGGC-3' (SEQ ID NO:13)
```

The amplified 2.6 kb fragment was digested with EcoRI and Hin-dIII, and ligated to EcoRI+HindIII digested pUC19. The ligation mixture was transformed, by electroporation, into E. coli SJ2 selecting ampicillin resistance (200 µg/ml) on IPTG X-gal plates. Six white colonies were picked for plasmid preparation. Three were correct, and could be digested with enzymes EcoRI, HindIII, SphI, NheI, SacII, SalI and BglII. One transformant was kept as SJ4465 (SJ2/pSJ4465).

Figure 24:
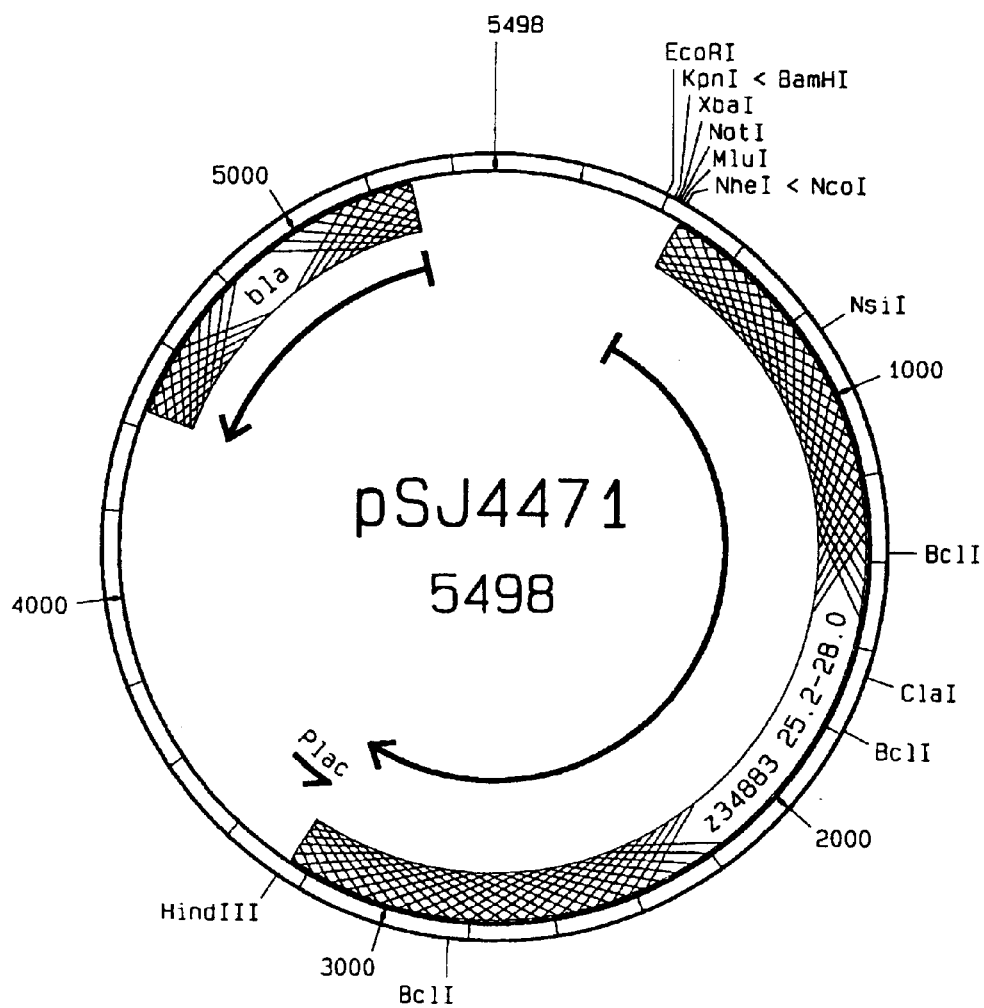

Plasmid pSJ4471 (FIG. 24) was constructed as follows:

Plasmid pSJ4461 was used as a substrate in a PCR reaction with primers #119887 and #119888, using 60° C. as annealing temperature and only 10 amplification cycles.

119887:

```
       XbaI   NotI   MluI  NheI NcoI <- z34883 25234-25260 ----->
5'-CAGTTCTAGAGCGGCCGCACGCGTGCTAGCCATGGCTTTTACAATAGAAGGAAAAGTCACCC 3' (SEQ ID NO:14)
```

119888:

```
       HindIII<- z34883 28038-28015 ->
5'-GACTAAGCTTCCTCTAACAGATTTCGAGGGGCAG-3' (SEQ ID NO:15)
```

The amplified 2.8 kb fragment was digested with XbaI and Hin-dIII, and ligated to XbaI+HindIII digested pUC19. The ligation mixture was transformed, by electroporation, into E. coli SJ2 selecting ampicillin resistance (200 µg/ml) on IPTG X-gal plates. 12 white colonies were picked for plasmid preparation. One was correct, and could be digested with enzymes XbaI, Hin-dIII, NotI, MluI, NheI, and NcoI. The strain was kept as SJ4471 (SJ2/pSJ4471).

Figure 25:
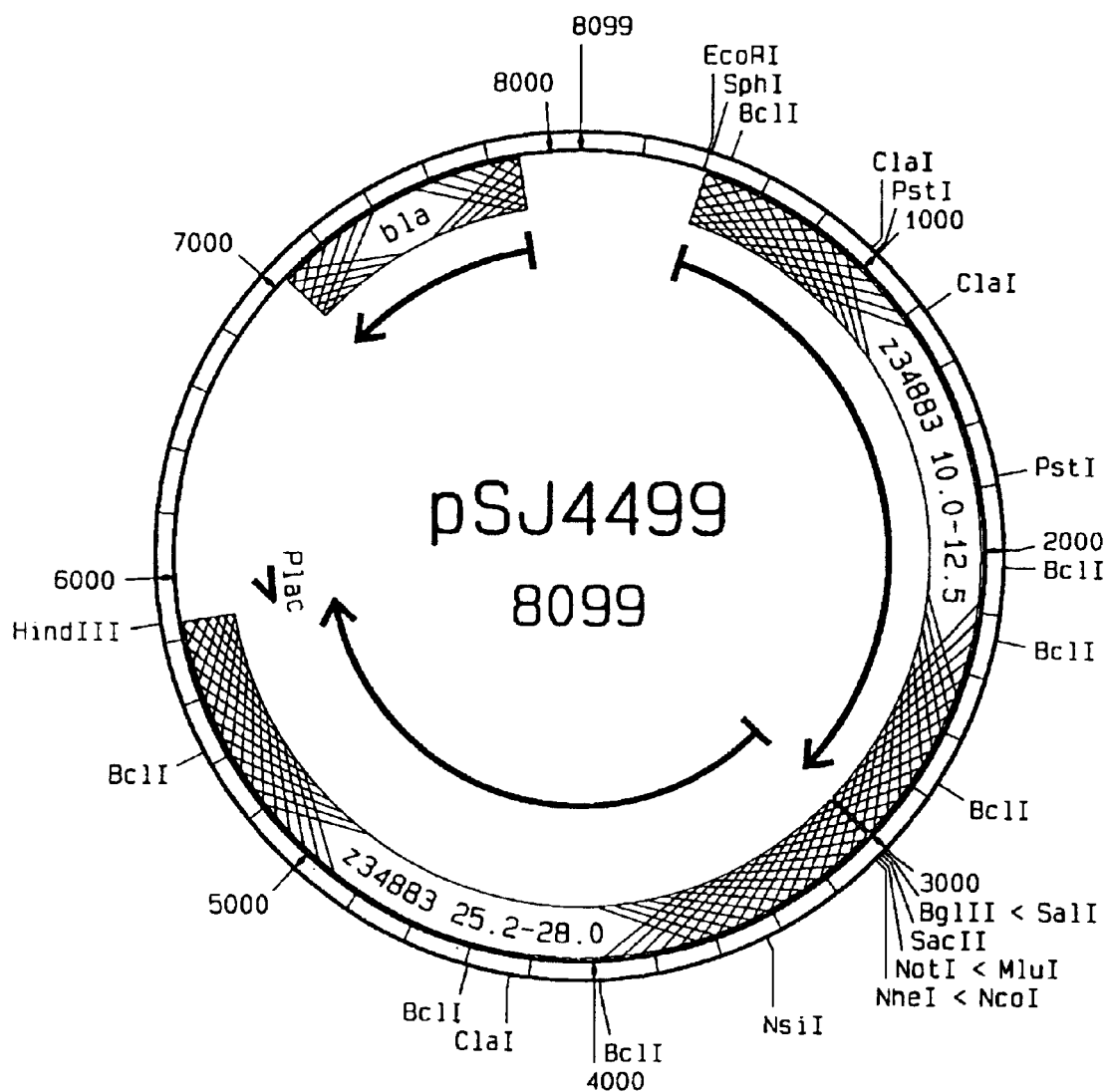

Plasmid pSJ4499 (FIG. 25) was constructed as follows:

Plasmid pSJ4465 was digested with EcoRI+NheI (+ with BsaI to further digest the unwanted part) and the 2.6 kb EcoRI-NheI fragment purified from an agarose gel. The fragment was ligated to EcoRI+XbaI digested pSJ4471, and the ligation mixture transformed (electroporation) into E. coli SJ6 selecting ampicillin resistance (200 µg/ml). A correct transformant was kept as SJ4499 (SJ6/pSJ4499).

Figure 26:
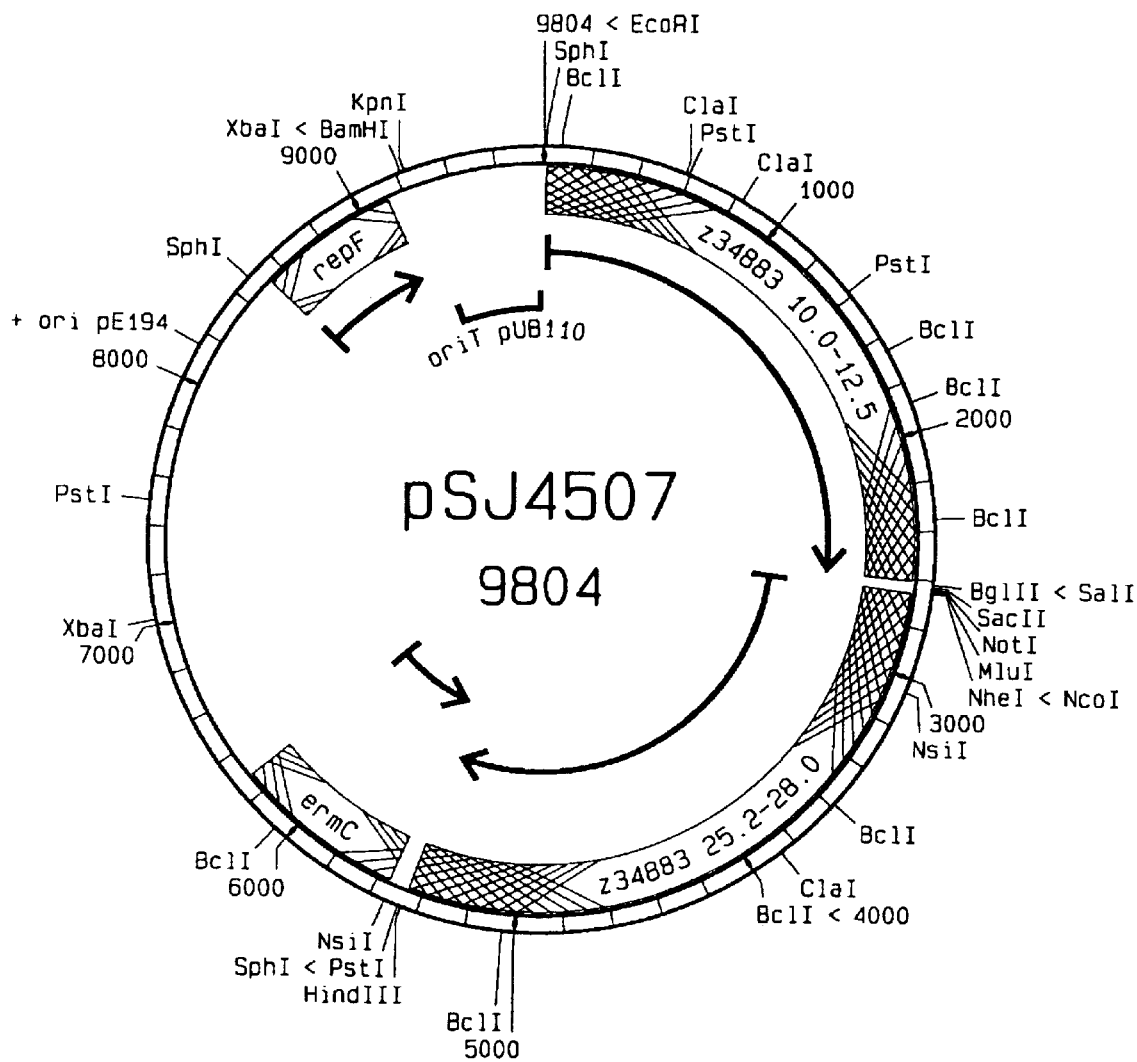

Plasmid pSJ4507 (FIG. 26) was constructed by digestion of pSJ4499 with EcoRI+HindIII, purification of the 5.4 kb fragment, and ligation to the 4.3 kb EcoRI-HindIII fragment of pSJ2739. The ligation mixture was transformed into B. subtilis DN1885 competent cells selecting erythromycin resistance (5 µg/ml) at 30° C. One transformant was kept as SJ4507 (DN1885/pSJ4507).

4C. Insertion of a gene encoding Bacillus licheniformis alpha-amylase, amyL into first and second integration vectors.

Figure 27:
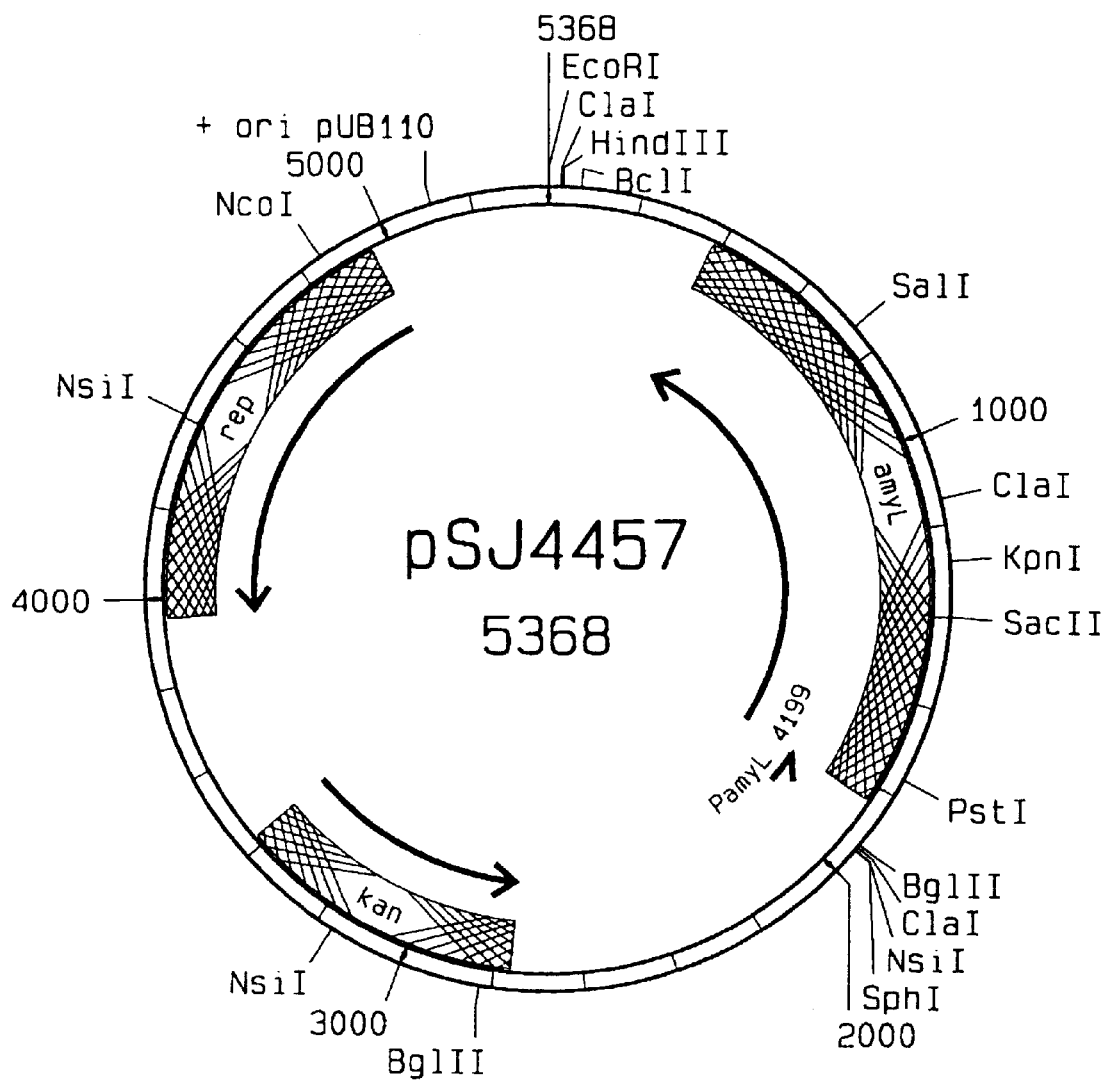

Plasmid pSJ4457 (FIG. 27) was constructed. This is almost identical to pSJ4277, previously described (FIG. 12) except for a few extra restriction sites upstream of the mutant amyL promoter. It was constructed by ligating the 0.2 kb SphI-PstI fragment purified from pSJ4338 (described in example 3A above, FIG. 13) to the 5 kb PstI-SphI fragment of pDN1981, and transformation of the ligation mixture into DN1885, selecting kanamycin (10 µg/ml) resistance. One transformant was kept as SJ4457 (DN1885/pSJ4457).

Figure 28:
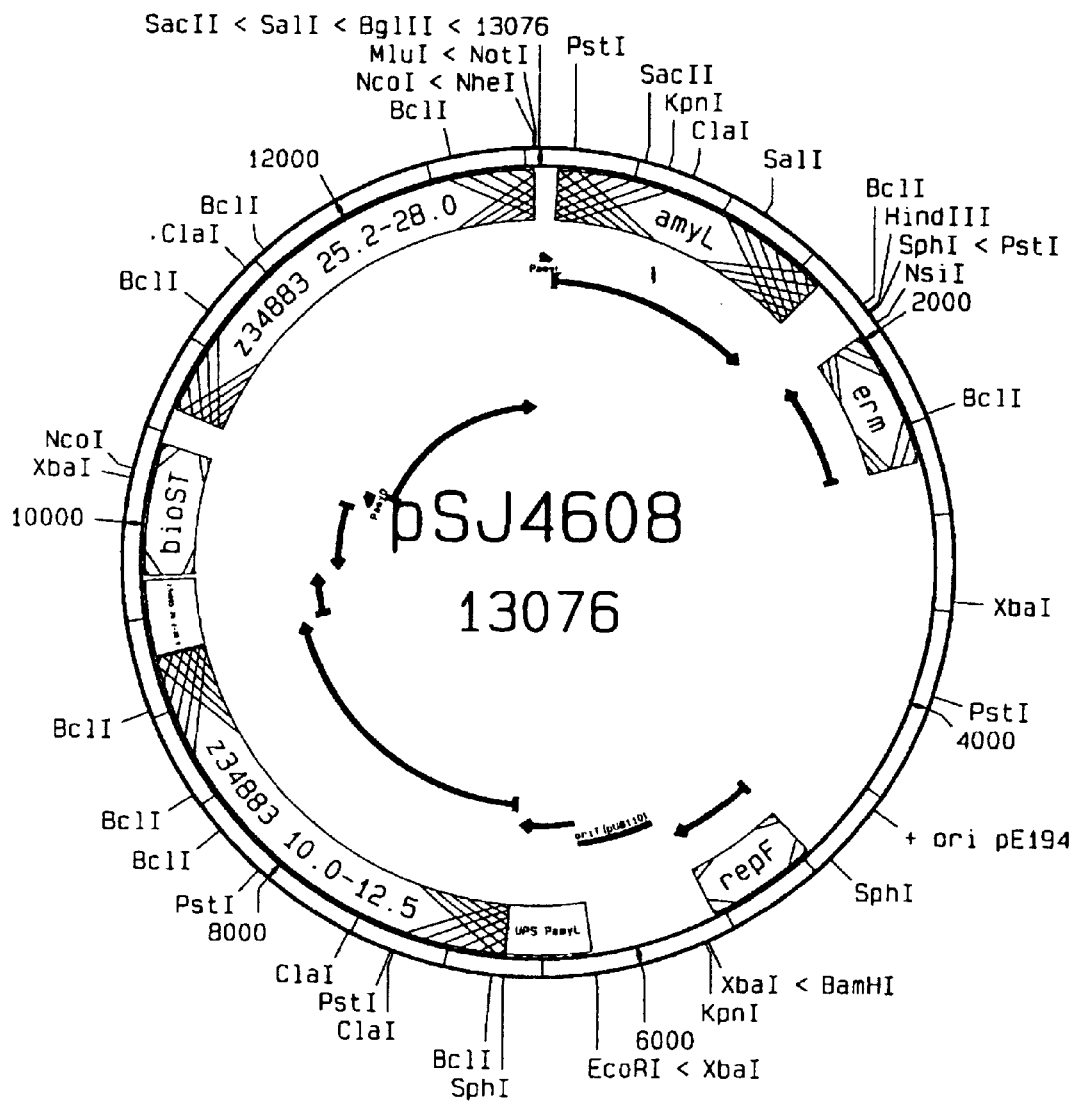

Plasmid pSJ4608 (FIG. 28) contains the amyL gene inserted into the first-copy integration vector, and was constructed as follows:

pSJ4457 was digested with BglII and HindIII, and the 1.9 kb fragment gel purified. This fragment was ligated to the 11.2 kb BglII-HindIII fragment from pSJ4587, and the ligation mixture transformed into competent DN1885 selecting erythromycin resistance (5 µg/ml) at 30° C. An amylase-positive, GFP positive transformant was kept as SJ4608 (DN1885/pSJ4608).

Figure 29:
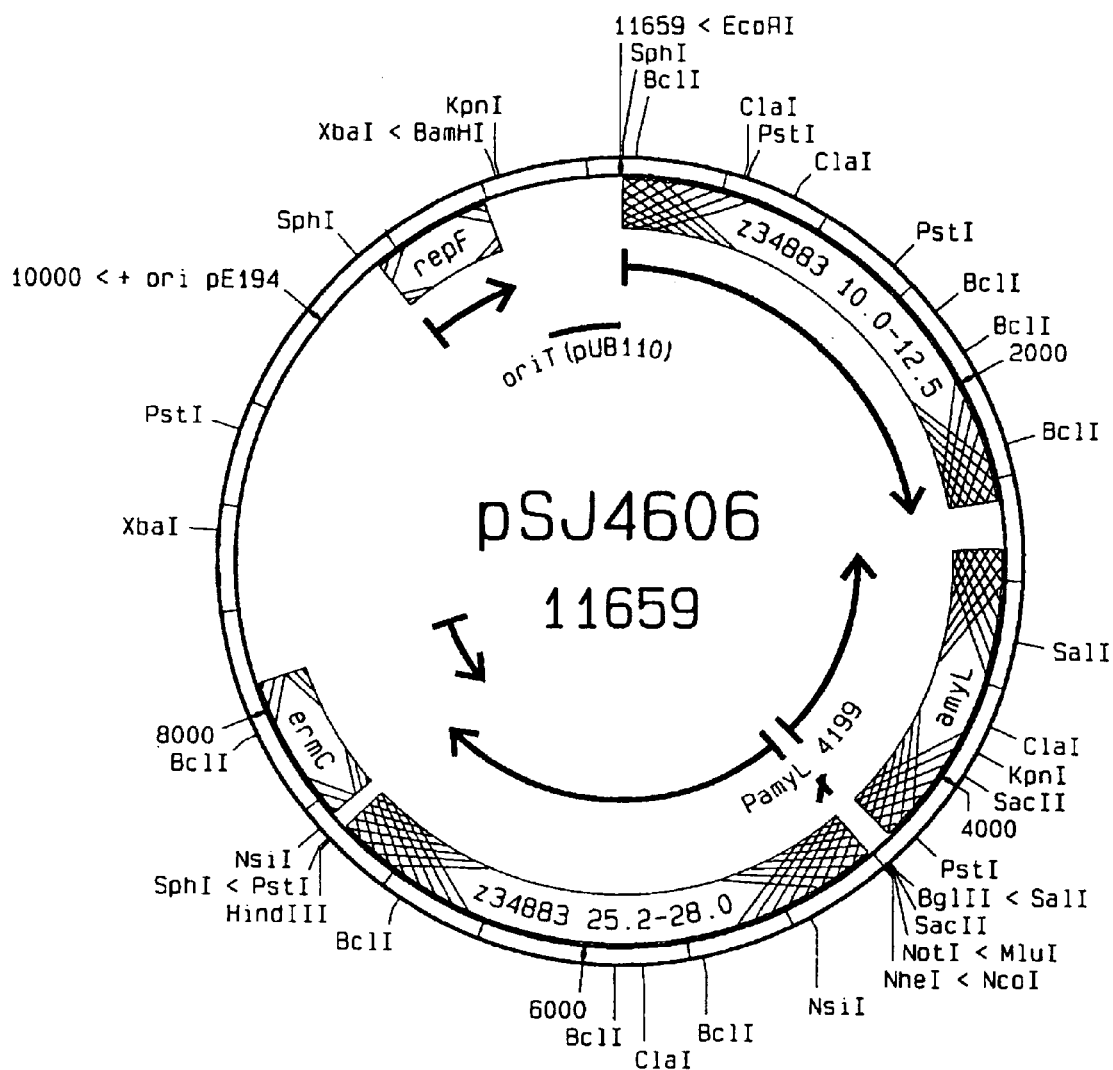

Plasmid pSJ4606 (FIG. 29) contains the amyL gene inserted into the second-copy integration vector, and was constructed as follows:

pSJ4457 was digested with BglII and BclI, and the 1.9 kb fragment gel purified. This fragment was ligated to BglII digested pSJ4507, and the ligation mixture transformed into competent DN1885 selecting erythromycin resistance (5 µg/ml) at 30° C. A transformant containing the amyL gene inserted in the desired orientation was kept as SJ4606 (DN1885/pSJ4606).

4D. Transfer to Bacillus licheniformis and chromosomal integration of first integration vector.

Plasmid pSJ4608 was transformed into competent cells of the conjugative donor host strain PP289-5, selecting for erythromycin (5 µg/ml) and tetracycline (5 µg/ml) resistance on LBPSG plates supplemented with D-alanine (100 µg/ml), and a transformant kept as SJ4611 (PP289-5/pSJ4608).

Plasmid pSJ4608 was transferred into B. licheniformis SJ3047 (described en example 1) by conjugation as previously described. An amylase positive, GFP positive transconjugant was streaked on an LBPSG plate with erythromycin (5 µg/ml) and incubated at 50° C. overnight. Six amylase positive, GFP positive colonies were inoculated into individual 10 ml TY cultures and shaken at 30° C. Cultures were then plated to single colonies on LBPSG at 30° C., and plates replica plated to LBPSG with erythromycin (5 µg/ml). Putative erythromycin sensitive, amylase positive colonies were reisolated. The GFP positive phenotype was clearly visible after about one week on the plates. Two amylase positive, GFP positive and erythromycin sensitive strains were kept as SJ4629 and SJ4630.

4E. Transfer to Bacillus licheniformis and chromosomal integration of second integration vector.

Plasmid pSJ4606 was transformed into competent cells of the conjugative donor host strain PP289-5, selecting for erythromycin (5 μg/ml) and tetracycline (5 μg/ml) resistance on LBPSG plates supplemented with D-alanine (100 μg/ml), and a transformant kept as SJ4609.

Plasmid pSJ4606 was transferred into B. licheniformis strains SJ4629 and SJ4630 by conjugation from SJ4609. Two transconjugants from each recipient were streaked on erythromycin (5 μg/ml) plates and incubated at 50° C. overnight. 12 colonies appearing at 50° C. from each recipient were inoculated into individual 10 ml TY cultures and shaken at 30° C. This propagation was repeated once. Cultures were then plated to single colonies on LBPSG at 30° C., and plates replica plated to LBPSG with erythromycin (5 μg/ml).

Erythromycin sensitive, GFP negative colonies were obtained from 12 of the 24 cultures.

Some strains kept were SJ4669, SJ4670 and SJ4671 (from separate TY cultures, from SJ4629 recipient), and SJ4672, SJ4673 and SJ4674 (from separate TY cultures, from SJ4630 recipient).

4F. Test of two-copy strains.

Strain SJ4270 (the single-copy strain), SJ4629 and SJ4630 (single-copy strains expressing also GFP, and containing the pps gene segments inserted), and the two-copy strains SJ4669-SJ4674 were tested in BPX shake flasks, incubated at 37° C. for one week, and α-amylase activity measured. The yield is expressed in percentage of the yield obtained with the control one-copy strain, SJ4270.

| Strain | Relative yield |
| --- | --- |
| SJ4270 (1) | 100 |
| SJ4270 (2) | 94 |
| SJ4629 (1) | 78 |
| SJ4629 (2) | 75 |
| SJ4630 (1) | 47 |
| SJ4630 (2) | 47 |
| SJ4669 | 163 |
| SJ4670 | 159 |
| SJ4671 | 159 |
| SJ4672 | 141 |
| SJ4673 | 143 |
| SJ4674 | 143 |

The surprisingly low yield obtained with strain SJ4630 was presumably due to a later detected contamination of this strain.

Strain SJ4671, which by Southern analysis (see below) was confirmed to harbour the two copies of the amyL gene inserted as intended, in opposite orientation, was chosen for further analysis by fermentation in a laboratory fermentor. On day 4 of the fermentation, a sample of the SJ4671 culture was plated on LBPG plates with dyed amylopectin to check for the amylase phenotype. The 800 colonies appearing were all amylase positive to the same extent, reflecting the stability of the strain.

10 of these colonies were inoculated into BPX shake flasks, with SJ4671 from the frozen stock via a plate as control, with the following result (7 days, 37° C.).

| Strain | Relative yield |
| --- | --- |
| SJ4671 | 100 |
| Colony 1 | 81 |
| Colony 2 | 94 |
| Colony 3 | 94 |
| Colony 4 | 88 |
| Colony 5 | 102 |
| Colony 6 | 96 |
| Colony 7 | 92 |
| Colony 8 | 106 |
| Colony 9 | 88 |
| Colony 10 | 90 |

The yield from SJ4671 in this experiment was 102% of the yield of SJ4671 obtained in the first experiment.

Thus, the single colonies picked after fermentation are all giving yields equivalent to the yield from the original SJ4671 strain, reflecting the stability of the strain.

4G. Southern analysis.

Chromosomal DNA from strains SJ3047, SJ4270, SJ4629, and two-copy strains, including SJ4671, was extracted and analysed by southern blot hybridizations. DNA preparations were digested with HindIII, or with HindIII+KpnI, and the DNA fragments separated by agarose gel electrophoresis were transferred to Immobilon-N (Millipore) membrane by vacuum blotting. The membrane was probed with biotinylated plasmid pDN1981 DNA, using the NE-Blot Photope Kit and Photope Detection Kit from New England Bio labs.

Plasmid pDN1981 used as probe contains the entire Termamyl gene (on a 2.4 kb SphI-HindIII fragment), the pUB110 origin and rep gene, and the kanamycin resistance gene.

The resulting blots reveals from strain SJ3047 a 4.2 kb HindIII fragment, as expected.

From strain SJ4270, a 3.3 kb HindIII fragment is revealed.
From strain SJ4629, a 9.6 kb HindIII fragment is revealed.
From strain SJ4671, 10.6 kb HindIII fragment is revealed.

Finally, strain SJ4671 DNA digested with both HindIII and KpnI reveals fragments of 5.2 kb, 4.2 kb and 1.3 kb.

This hybridization pattern is as expected from the desired two-copy strain, confirming the correctness of strain SJ4671.

I claim:

1. A prokaryotic cell expressing a gene of interest in that, said cell comprising two copies of said gene of interest on a single chromosome, wherein (i) the gene copies are oriented with respect to each other so that transcription from the gene copies is antiparallel; and ii) any DNA segment situated between the gene copies is not essential for the growth of the cell.

2. A method for constructing a prokaryotic cell expressing a gene of interest, said method comprising introducing two copies of the gene into a single chromosome of the cell, wherein
   (i) the gene copies are oriented with respect to each other so that transcription from the gene copies is antiparallel; and
   ii) any DNA segment situated between the gene copies is not essential for the growth of the cell.

3. The prokaryotic cell according to claim 1 wherein said gene of interest is a gene which is capable of expressing a polypeptide which is secreted from the cell.

4. The prokaryotic cell according to claim 1, wherein said gene encodes an enzyme.

5. The prokaryotic cell according to claim 1, wherein said prokaryotic cell is a Bacillus cell.

6. The prokaryotic cell according to claim 1, wherein said DNA segment situated between the two gene copies is at least 10 bp long.

7. The prokaryotic cell according to claim 1, wherein said DNA segment situated between the two gene copies does not comprise an antibiotic resistance marker gene.

8. A method for production and isolation of a polypeptide of interest, comprising
   i) culturing a prokaryotic cell according to claim 1 under suitable conditions permitting expression of the polypeptide of interest encoded by the gene of interest; and
   ii) isolating the polypeptide of interest.

9. The method for production and isolation of a polypeptide of interest of claim 8, wherein the polypeptide of interest is expressed in an amount of at least 2 g polypeptide (dry matter)/kg culture medium.

10. The method for production and isolation of a polypeptide of interest of claim 8, wherein the culturing is performed on a volume scale which is >10 m$^3$.

* * * * *

SEQUENCE LISTING

<160> NUMBER OF SEQ ID NOS: 15

<210> SEQ ID NO 1
<211> LENGTH: 63
<212> TYPE: DNA
<213> ORGANISM: Bacillus licheniformis

<400> SEQUENCE: 1

```
tgagtaagct tggtaccctg caggctagcg catgcgctga gatacagtta ccaattgata      60
gcc                                                                   63

<210> SEQ ID NO 2
<211> LENGTH: 43
<212> TYPE: DNA
<213> ORGANISM: Bacillus licheniformis

<400> SEQUENCE: 2
tgagtgaatt ctctagacct tctttgtgct tggaagcaga gcc                        43

<210> SEQ ID NO 3
<211> LENGTH: 20
<212> TYPE: DNA
<213> ORGANISM: Bacillus licheniformis

<400> SEQUENCE: 3
ctgctgcgac atcaggatgg                                                  20

<210> SEQ ID NO 4
<211> LENGTH: 20
<212> TYPE: DNA
<213> ORGANISM: Bacillus licheniformis

<400> SEQUENCE: 4
catggacttc atttactggg                                                  20

<210> SEQ ID NO 5
<211> LENGTH: 107
<212> TYPE: DNA
<213> ORGANISM: Bacillus licheniformis

<400> SEQUENCE: 5
gctctagagc atgctggaag aaaatatagg gaaaatggta cttgttaaaa attcggaata      60
tttatacaat atcatatgta tcacattgaa aggggaggag aatcatg                   107

<210> SEQ ID NO 6
<211> LENGTH: 20
<212> TYPE: DNA
<213> ORGANISM: Bacillus licheniformis

<400> SEQUENCE: 6
gctgctgcag aatgaggcag                                                  20

<210> SEQ ID NO 7
<211> LENGTH: 39
<212> TYPE: DNA
<213> ORGANISM: Bacillus licheniformis

<400> SEQUENCE: 7
gtcagcatgc atcgatagat cttggaagaa aatatagg                              39

<210> SEQ ID NO 8
<211> LENGTH: 20
<212> TYPE: DNA
<213> ORGANISM: Bacillus licheniformis

<400> SEQUENCE: 8
gctgctgcag aatgaggcag                                                  20

<210> SEQ ID NO 9
```

```
<211> LENGTH: 38
<212> TYPE: DNA
<213> ORGANISM: B. subtilis

<400> SEQUENCE: 9
cagtgaattc gcatgcagca ggtagttcta tcaaaccg                              38

<210> SEQ ID NO 10
<211> LENGTH: 40
<212> TYPE: DNA
<213> ORGANISM: B. subtilis

<400> SEQUENCE: 10
gactaagctt gctagccgct ggatgttaat ggcatctggc                           40

<210> SEQ ID NO 11
<211> LENGTH: 37
<212> TYPE: DNA
<213> ORGANISM: B. subtilis

<400> SEQUENCE: 11
cagttctaga cttttacaat agaaggaaaa gtcaccc                              37

<210> SEQ ID NO 12
<211> LENGTH: 75
<212> TYPE: DNA
<213> ORGANISM: B. subtilis

<400> SEQUENCE: 12
gactaagctt agatctgagc tccgcggcgg ccgcacgcgt gctagccatg gcctctaaca     60
gatttcgagg ggcag                                                      75

<210> SEQ ID NO 13
<211> LENGTH: 58
<212> TYPE: DNA
<213> ORGANISM: B. subtilis

<400> SEQUENCE: 13
gactaagctt gctagccgcg gagctcagat ctgccgctgg atgttaatgg catctggc      58

<210> SEQ ID NO 14
<211> LENGTH: 62
<212> TYPE: DNA
<213> ORGANISM: B. subtilis

<400> SEQUENCE: 14
cagttctaga gcggccgcac gcgtgctagc catggctttt acaatagaag gaaaagtcac     60
cc                                                                    62

<210> SEQ ID NO 15
<211> LENGTH: 34
<212> TYPE: DNA
<213> ORGANISM: B. subtilis

<400> SEQUENCE: 15
gactaagctt cctctaacag atttcgaggg gcag                                 34
```